(12) United States Patent
Lief et al.

(10) Patent No.: US 10,336,663 B2
(45) Date of Patent: Jul. 2, 2019

(54) METHODS FOR THE PREPARATION AND USE OF SUSPENSIONS OF CHEMICALLY-TREATED SOLID OXIDES IN AN OLEFIN-DERIVED LIQUID MEDIUM

(71) Applicant: Chevron Phillips Chemical Company LP, The Woodlands, TX (US)

(72) Inventors: Graham R. Lief, Bartlesville, OK (US); Eric J. Haschke, Bartlesville, OK (US); Pasquale Iacono, Bartlesville, OK (US)

(73) Assignee: Chevron Phillips Chemical Company LP, The Woodlands, TX (US)

( * ) Notice: Subject to any disclaimer, the term of this patent is extended or adjusted under 35 U.S.C. 154(b) by 49 days.

(21) Appl. No.: 15/701,577

(22) Filed: Sep. 12, 2017

(65) Prior Publication Data
US 2019/0077727 A1 Mar. 14, 2019

(51) Int. Cl.
| | |
|---|---|
| C07C 2/04 | (2006.01) |
| C07C 2/06 | (2006.01) |
| C07C 2/08 | (2006.01) |
| C07C 2/10 | (2006.01) |
| C07C 5/03 | (2006.01) |
| C07C 5/05 | (2006.01) |
| C07C 2/32 | (2006.01) |
| B01J 31/14 | (2006.01) |
| B01J 31/22 | (2006.01) |
| B01J 8/18 | (2006.01) |
| B01J 21/12 | (2006.01) |

(52) U.S. Cl.
CPC .............. *C07C 2/32* (2013.01); *B01J 8/1836* (2013.01); *B01J 21/12* (2013.01); *B01J 31/143* (2013.01); *B01J 31/2295* (2013.01); *C07C 5/05* (2013.01); *B01J 2231/20* (2013.01); *B01J 2531/48* (2013.01); *B01J 2531/49* (2013.01); *C07C 2531/16* (2013.01)

(58) Field of Classification Search
USPC .................. 585/258, 519, 521, 530, 517
See application file for complete search history.

(56) References Cited

U.S. PATENT DOCUMENTS

| | | | |
|---|---|---|---|
| 6,107,230 A | 8/2000 | McDaniel et al. | |
| 6,165,929 A | 12/2000 | McDaniel et al. | |
| 6,294,494 B1 | 9/2001 | McDaniel et al. | |
| 6,300,271 B1 | 10/2001 | McDaniel et al. | |
| 6,316,553 B1 | 11/2001 | McDaniel et al. | |
| 6,355,594 B1 | 3/2002 | McDaniel et al. | |
| 6,376,415 B1 | 4/2002 | McDaniel et al. | |
| 6,388,017 B1 | 5/2002 | McDaniel et al. | |
| 6,391,816 B1 | 5/2002 | McDaniel et al. | |
| 6,395,666 B1 | 5/2002 | McDaniel et al. | |
| 6,524,987 B1 | 2/2003 | Collins et al. | |
| 6,548,441 B1 | 4/2003 | McDaniel et al. | |
| 6,548,442 B1 | 4/2003 | McDaniel et al. | |
| 6,576,583 B1 | 6/2003 | McDaniel et al. | |
| 6,613,712 B1 | 9/2003 | McDaniel et al. | |
| 6,632,894 B1 | 10/2003 | McDaniel et al. | |
| 6,667,274 B1 * | 12/2003 | Hawley ................ | C08F 110/06 502/102 |
| 6,750,302 B1 | 6/2004 | McDaniel et al. | |
| 7,026,494 B1 | 4/2006 | Yang et al. | |
| 7,041,617 B2 | 5/2006 | Jensen et al. | |
| 7,199,073 B2 | 4/2007 | Martin et al. | |
| 7,226,886 B2 | 6/2007 | Jayaratne et al. | |
| 7,294,599 B2 | 11/2007 | Jensen et al. | |
| 7,312,283 B2 | 12/2007 | Martin et al. | |
| 7,517,939 B2 | 4/2009 | Yang et al. | |
| 7,601,665 B2 | 10/2009 | McDaniel et al. | |
| 7,619,047 B2 | 11/2009 | Yang et al. | |
| 7,884,163 B2 | 2/2011 | McDaniel et al. | |
| 8,309,485 B2 | 11/2012 | Yang et al. | |
| 8,623,973 B1 | 1/2014 | McDaniel et al. | |
| 8,703,886 B1 | 4/2014 | Yang et al. | |
| 9,023,959 B2 | 5/2015 | McDaniel et al. | |
| 9,303,106 B1 | 4/2016 | Clark et al. | |
| 9,611,188 B1 | 4/2017 | Yang et al. | |
| 9,631,158 B2 | 4/2017 | Yang et al. | |
| 9,707,549 B1 | 7/2017 | Kilgore et al. | |
| 9,732,300 B2 | 8/2017 | Kilgore et al. | |
| 9,745,230 B2 | 8/2017 | Small et al. | |
| 9,890,093 B2 | 2/2018 | Yang et al. | |
| 2017/0174584 A1 | 6/2017 | Yang et al. | |
| 2018/0044446 A1 | 2/2018 | Lief et al. | |

FOREIGN PATENT DOCUMENTS

WO    WO 2010/147993    12/2010

* cited by examiner

*Primary Examiner* — Thuan D Dang
(74) *Attorney, Agent, or Firm* — Merchant & Gould P.C.

(57) ABSTRACT

The present invention discloses processes for oligomerizing an olefin feedstock containing $C_4$ to $C_{20}$ alpha olefins using a catalyst system containing a metallocene compound, an organoaluminum compound, and a suspension of a chemically-treated solid oxide. The liquid medium for the suspension of the chemically-treated solid oxide can be an alpha-olefin oligomer product formed by the oligomerization process.

22 Claims, No Drawings

METHODS FOR THE PREPARATION AND USE OF SUSPENSIONS OF CHEMICALLY-TREATED SOLID OXIDES IN AN OLEFIN-DERIVED LIQUID MEDIUM

BACKGROUND OF THE INVENTION

The present invention relates generally to processes for oligomerizing olefins using catalyst systems containing a chemically-treated solid oxide. In certain oligomerization processes, the liquid medium for the chemically-treated solid oxide can be an alpha-olefin oligomer product.

SUMMARY OF THE INVENTION

This summary is provided to introduce a selection of concepts in a simplified form that are further described herein. This summary is not intended to identify required or essential features of the claimed subject matter. Nor is this summary intended to be used to limit the scope of the claimed subject matter.

Processes relating to the oligomerization of olefins are disclosed and described herein. One such process can comprise (a) contacting a first olefin feedstock comprising a first $C_4$-$C_{20}$ alpha-olefin with a first catalyst system in a first reaction zone to form a first oligomer product, (b) discharging a first reaction zone effluent comprising the first oligomer product from the first reaction zone, (c) optionally deactivating the first catalyst system to form a deactivated first catalyst system, and isolating an effluent fraction by removing at least a portion of the first catalyst system or the deactivated first catalyst system from the first reaction zone effluent, (d) isolating the first oligomer product by removing at least a portion of unreacted first $C_4$-$C_{20}$ alpha-olefin from the effluent fraction, (e) contacting a suspension of a second chemically treated solid oxide in a liquid medium, a second metallocene compound, a second organoaluminum compound, and a second olefin feedstock comprising a second $C_4$-$C_{20}$ alpha-olefin, in a second reaction zone to form a second oligomer product, wherein the liquid medium comprises at least a portion of the effluent fraction and/or at least a portion of the first oligomer product, (f) discharging a second reaction zone effluent comprising the second oligomer product from the second reaction zone, the second oligomer product comprising a light fraction comprising $C_{26}$ and lower oligomers (e.g., $C_8$-$C_{26}$), and a heavy oligomer product comprising $C_{28}$ and higher oligomers, (g) isolating the heavy oligomer product from the second oligomer product, and (h) hydrogenating at least a portion of the heavy oligomer product to produce a hydrogenated heavy oligomer product.

Another process relating to the oligomerization of olefins is disclosed and described herein, and in this aspect, the process can comprise (A) contacting a first olefin feedstock comprising a first $C_4$-$C_{20}$ alpha-olefin with a first catalyst system in a first reaction zone to form a first oligomer product, (B) discharging a first reaction zone effluent comprising the first oligomer product from the first reaction zone, the first oligomer product comprising a first light fraction comprising $C_{26}$ and lower oligomers (e.g., $C_8$-$C_{26}$), and a first heavy oligomer product comprising $C_{28}$ and higher oligomers, (C) isolating the first light fraction and isolating the first heavy oligomer product from the first oligomer product, (D) hydrogenating at least a portion of the first heavy oligomer product to produce a first hydrogenated heavy oligomer product, (E) contacting a suspension of a second chemically-treated solid oxide in a liquid medium, a second metallocene compound, a second organoaluminum compound, and a second olefin feedstock comprising a second $C_4$-$C_{20}$ alpha-olefin, in a second reaction zone to form a second oligomer product, wherein the liquid medium comprises at least a portion of one or more of the first light fraction, the first heavy oligomer product, the first hydrogenated heavy oligomer product, or any combination thereof, (F) discharging a second reaction zone effluent comprising the second oligomer product from the second reaction zone, the second oligomer product comprising a second light fraction comprising $C_{26}$ and lower oligomers (e.g., $C_8$-$C_{26}$), and a second heavy oligomer product comprising $C_{28}$ and higher oligomers, (G) isolating the second heavy oligomer product from the second oligomer product, and (H) hydrogenating at least a portion the second heavy oligomer product to produce a second hydrogenated heavy oligomer product.

Suspension compositions containing a $C_4$-$C_{20}$ alpha-olefin oligomer product and from 1 to 30 wt. % of a chemically-treated solid oxide also are disclosed and described herein. In some aspects, the composition also can contain an organoaluminum compound. Generally, the alpha-olefin oligomer product can have a 100° C. kinematic viscosity ranging from 2 to 200 cSt.

Both the foregoing summary and the following detailed description provide examples and are explanatory only. Accordingly, the foregoing summary and the following detailed description should not be considered to be restrictive. Further, features or variations may be provided in addition to those set forth herein. For example, certain aspects may be directed to various feature combinations and sub-combinations described in the detailed description.

DEFINITIONS

To define more clearly the terms used herein, the following definitions are provided. Unless otherwise indicated, the following definitions are applicable to this disclosure. If a term is used in this disclosure but is not specifically defined herein, the definition from the IUPAC Compendium of Chemical Terminology, 2nd Ed (1997), can be applied, as long as that definition does not conflict with any other disclosure or definition applied herein, or render indefinite or non-enabled any claim to which that definition is applied. To the extent that any definition or usage provided by any document incorporated herein by reference conflicts with the definition or usage provided herein, the definition or usage provided herein controls.

Herein, features of the subject matter can be described such that, within particular aspects, a combination of different features can be envisioned. For each and every aspect and/or feature disclosed herein, all combinations that do not detrimentally affect the designs, compositions, processes, and/or methods described herein are contemplated with or without explicit description of the particular combination. Additionally, unless explicitly recited otherwise, any aspect and/or feature disclosed herein can be combined to describe inventive features consistent with the present disclosure.

While compositions and methods are described in terms of "comprising" various components or steps, the compositions and methods can also "consist essentially of" or "consist of" the various components or steps, unless specifically stated otherwise. For example, a catalyst system consistent with aspects of the present invention can comprise; alternatively, can consist essentially of; or alternatively, can consist of; a metallocene compound, a chemically-treated solid oxide, and an organoaluminum compound.

The terms "a," "an," and "the" are intended to include plural alternatives, e.g., at least one, unless otherwise specified. For instance, the disclosure of "a chemically-treated solid oxide" or "a metallocene compound" is meant to encompass one, or mixtures or combinations of more than one, chemically-treated solid oxide or metallocene compound, respectively, unless otherwise specified.

Generally, groups of elements are indicated using the numbering scheme indicated in the version of the periodic table of elements published in Chemical and Engineering News, 63(5), 27, 1985. In some instances, a group of elements can be indicated using a common name assigned to the group; for example, alkali metals for Group 1 elements, alkaline earth metals for Group 2 elements, transition metals for Group 3-12 elements, and halogens or halides for Group 17 elements.

For any particular compound or group disclosed herein, any name or structure presented is intended to encompass all conformational isomers, regioisomers, stereoisomers, and mixtures thereof that can arise from a particular set of substituents, unless otherwise specified. The name or structure also encompasses all enantiomers, diastereomers, and other optical isomers (if there are any), whether in enantiomeric or racemic forms, as well as mixtures of stereoisomers, as would be recognized by a skilled artisan, unless otherwise specified. For example, a general reference to hexene (or hexenes) includes all linear or branched, acyclic or cyclic, hydrocarbon compounds having six carbon atoms and 1 carbon-carbon double bond; a general reference to pentane includes n-pentane, 2-methyl-butane, and 2,2-dimethylpropane; a general reference to a butyl group includes an n-butyl group, a sec-butyl group, an iso-butyl group, and a t-butyl group; a general reference to cyclododecatriene includes all isomeric forms (e.g., trans,trans,cis-1,5,9-cyclododecatriene, and trans,trans,trans-1,5,9-cyclododecatriene, among other dodecatrienes); and a general reference to 2,3-pentanediol includes 2R,3R-pentanediol, 2S,3S-pentanediol, 2R,3S-pentanediol, and mixtures thereof.

The term "contacting" is used herein to describe methods, processes, and compositions wherein the components are contacted or combined together in any order, in any manner, and for any length of time, unless otherwise specified. For example, the components can be contacted by blending or mixing. Further, unless otherwise specified, the contacting of any component can occur in the presence or absence of any other component of the methods, processes, and compositions described herein. Combining additional materials or components can be done by any suitable technique. Further, "contacting" two or more components can result in a solution, a slurry, a mixture, a reaction mixture, or a reaction product.

The term "hydrocarbon" whenever used in this specification and claims refers to a compound containing only carbon and hydrogen atoms. The term "olefin" as used herein refers to a hydrocarbon that has at least one carbon-carbon double bond that is not part of an aromatic ring or ring system. The term "olefin" includes aliphatic and aromatic, cyclic and acyclic, and/or linear and branched compounds having at least one carbon-carbon double bond that is not part of an aromatic ring or ring system, unless specifically stated otherwise. Olefins having only one, only two, only three, etc., carbon-carbon double bonds can be identified by use of the term "mono," "di," "tri," etc., within the name of the olefin. The olefins can be further identified by the position of the carbon-carbon double bond(s). The term "alpha olefin" as used herein refers to any olefin that has a double bond between the first and second carbon atom of a contiguous chain of carbon atoms. The term "alpha olefin" includes linear and branched alpha olefins and alpha olefins which have more than one non-aromatic carbon-carbon double bond, unless expressly stated otherwise. The term "normal alpha olefin" as used herein refers to a linear hydrocarbon mono-olefin having a double bond between the first and second carbon atom.

In this disclosure, "reaction zone effluent" includes the overall composition that is discharged from an olefin oligomerization reaction zone, while "effluent fraction" generally refers to the effluent in which all or a portion of the catalyst system (whether deactivated, or not) has been removed. While not being limited thereto, the effluent fraction often can have a 100° C. kinematic viscosity from 2 to 200 cSt. An "oligomer product" refers to the effluent fraction after all or a portion of unreacted alpha-olefin monomer has been removed. While not being limited thereto, the oligomer product often can have a 100° C. kinematic viscosity from 2 to 200 cSt. A "light fraction" and a "heavy oligomer product" can be isolated from the oligomer product. The "light fraction" is predominantly $C_{26}$ and lower oligomers (e.g., $C_8$-$C_{26}$), and often can have a 100° C. kinematic viscosity of less than or equal to 10 cSt, while the "heavy oligomer product" is predominantly $C_{28}$ and higher oligomers, and often can have a 100° C. kinematic viscosity from 2 to 200 cSt. After hydrogenation, the heavy oligomer product is referred to as a "hydrogenated heavy oligomer product" (or a polyalphaolefin, PAO). These terms are also used generically herein to include alpha-olefin homo-oligomers, alpha-olefin co-oligomers, and so forth, and thus encompass products derived from any number of different olefin monomers disclosed herein. In like manner, oligomerizing (or oligomerization) is meant to encompasses dimerizing (or dimerization), trimerizing (or trimerization), and so forth.

The term "about" means that amounts, sizes, formulations, parameters, and other quantities and characteristics are not and need not be exact, but can be approximate including being larger or smaller, as desired, reflecting tolerances, conversion factors, rounding off, measurement errors, and the like, and other factors known to those of skill in the art. In general, an amount, size, formulation, parameter or other quantity or characteristic is "about" or "approximate" whether or not expressly stated to be such. The term "about" also encompasses amounts that differ due to different equilibrium conditions for a composition resulting from a particular initial mixture. Whether or not modified by the term "about," the claims include equivalents to the quantities. The term "about" can mean within 10% of the reported numerical value, preferably within 5% of the reported numerical value.

Although any methods and materials similar or equivalent to those described herein can be used in the practice or testing of the invention, the typical methods and materials are herein described.

All publications and patents mentioned herein are incorporated herein by reference for the purpose of describing and disclosing, for example, the constructs and methodologies that are described in the publications, which might be used in connection with the presently described invention.

DETAILED DESCRIPTION OF THE INVENTION

Olefin oligomerization processes using catalyst systems containing a chemically-treated solid oxide are disclosed herein. In these oligomerization processes, the liquid medium (or carrier, or suspending agent) for the chemically-treated solid oxide can be a product fraction produced by the oligomerization process.

One potential benefit of using a suspension of the chemically-treated solid oxide in the liquid medium, as opposed to solids conveying, is improved consistency and accuracy of chemically-treated solid oxide addition or metering to a catalyst preparation vessel and/or to an oligomerization reaction zone, ultimately resulting in improved consistency of the oligomerization process. Another potential benefit of using a suspension of the chemically-treated solid oxide in the liquid medium, in which the liquid medium is a product fraction produced by the oligomerization process (and used as a carrier for the chemically-treated solid oxide), is that an extra separations step is not needed or required to remove the liquid medium from the reactor effluent, since the liquid medium is compatible and is an alpha-olefin oligomer product (e.g., and not a non-olefin aromatic or aliphatic hydrocarbon carrier). Further, another potential benefit of using a suspension of the chemically-treated solid oxide in the liquid medium, in which the liquid medium is a product fraction produced by the oligomerization process (and used as a carrier for the chemically-treated solid oxide), is the reduction in the amount of non-olefin materials added to the reaction zone prior to and during oligomerization. Accordingly, the product quality can be improved using the processes disclosed herein. Other potential benefits of the disclosed processes are readily apparent from this disclosure.

Olefin Oligomerization Processes

Aspects of this invention are directed to oligomerization processes. In accordance with an aspect of this invention, a first process can comprise (or consist essentially of, or consist of) (a) contacting a first olefin feedstock comprising a first $C_4$-$C_{20}$ alpha-olefin with a first catalyst system in a first reaction zone to form a first oligomer product; (b) discharging a first reaction zone effluent comprising the first oligomer product from the first reaction zone; (c) optionally deactivating the first catalyst system to form a deactivated first catalyst system, and isolating an effluent fraction by removing at least a portion of the first catalyst system or the deactivated first catalyst system from the first reaction zone effluent; (d) isolating the first oligomer product by removing at least a portion of unreacted first $C_4$-$C_{20}$ alpha-olefin from the effluent fraction; (e) contacting a suspension of a second chemically-treated solid oxide in a liquid medium, a second metallocene compound, a second organoaluminum compound, and a second olefin feedstock comprising a second $C_4$-$C_{20}$ alpha-olefin, in a second reaction zone to form a second oligomer product, wherein the liquid medium comprises at least a portion of the effluent fraction and/or at least a portion of the first oligomer product; (f) discharging a second reaction zone effluent comprising the second oligomer product from the second reaction zone, the second oligomer product comprising a light fraction comprising $C_{26}$ and lower oligomers (e.g., $C_8$-$C_{26}$), and a heavy oligomer product comprising $C_{28}$ and higher oligomers; (g) isolating the heavy oligomer product from the second oligomer product; and (h) hydrogenating at least a portion of the heavy oligomer product to produce a hydrogenated heavy oligomer product.

In a further aspect of this first process, the liquid medium can comprise at least a portion of the effluent fraction. For example, at least 25 wt. %, at least 50 wt. %, at least 75 wt. %, at least 80 wt. %, at least 90 wt. %, at least 95 wt. %, at least 98 wt. %, or 100 wt. %, of the liquid medium can be a portion of the effluent fraction. Alternatively, the liquid medium can comprise at least a portion of the first oligomer product, for instance, at least 25 wt. %, at least 50 wt. %, at least 75 wt. %, at least 80 wt. %, at least 90 wt. %, at least 95 wt. %, at least 98 wt. %, or 100 wt. %, of the liquid medium can be a portion of the first oligomer product. Additionally, mixtures of portions of the effluent fraction and the first oligomer product can be used as the liquid medium, and at any suitable blend ratio.

In accordance with another aspect of this invention, a second process can comprise (or consist essentially of, or consist of) (A) contacting a first olefin feedstock comprising a first $C_4$-$C_{20}$ alpha-olefin with a first catalyst system in a first reaction zone to form a first oligomer product; (B) discharging a first reaction zone effluent comprising the first oligomer product from the first reaction zone, the first oligomer product comprising a first light fraction comprising $C_{26}$ and lower oligomers (e.g., $C_8$-$C_{26}$), and a first heavy oligomer product comprising $C_{28}$ and higher oligomers; (C) isolating the first light fraction and isolating the first heavy oligomer product from the first oligomer product; (D) hydrogenating at least a portion of the first heavy oligomer product to produce a first hydrogenated heavy oligomer product; (E) contacting a suspension of a second chemically-treated solid oxide in a liquid medium, a second metallocene compound, a second organoaluminum compound, and a second olefin feedstock comprising a second $C_4$-$C_{20}$ alpha-olefin, in a second reaction zone to form a second oligomer product, wherein the liquid medium comprises at least a portion of one or more of the first light fraction, the first heavy oligomer product, the first hydrogenated heavy oligomer product, or any combination thereof; (F) discharging a second reaction zone effluent comprising the second oligomer product from the second reaction zone, the second oligomer product comprising a second light fraction comprising $C_{26}$ and lower oligomers (e.g., $C_8$-$C_{26}$), and a second heavy oligomer product comprising $C_{28}$ and higher oligomers; (G) isolating the second heavy oligomer product from the second oligomer product; and (H) hydrogenating at least a portion the second heavy oligomer product to produce a second hydrogenated heavy oligomer product.

In a further aspect of this second process, the liquid medium can comprise at least a portion of the first light fraction; alternatively, at least a portion of the first heavy oligomer product; or alternatively, at least a portion of the first hydrogenated heavy oligomer product. Thus, at least 25 wt. %, at least 50 wt. %, at least 75 wt. %, at least 80 wt. %, at least 90 wt. %, at least 95 wt. %, at least 98 wt. %, or 100 wt. %, of the liquid medium can be a portion of the first light fraction. Additionally or alternatively, at least 25 wt. %, at least 50 wt. %, at least 75 wt. %, at least 80 wt. %, at least 90 wt. %, at least 95 wt. %, at least 98 wt. %, or 100 wt. %, of the liquid medium can be a portion of the first heavy oligomer product. Additionally or alternatively, at least 25 wt. %, at least 50 wt. %, at least 75 wt. %, at least 80 wt. %, at least 90 wt. %, at least 95 wt. %, at least 98 wt. %, or 100 wt. %, of the liquid medium can be a portion of the first hydrogenated heavy oligomer product. Further, mixtures of portions of the first light fraction, the first heavy oligomer product, and the first hydrogenated heavy oligomer product can be used as the liquid medium, and at any suitable blend ratio.

Generally, the features of the first and second processes (e.g., the components and/or features of the (first or second) olefin feedstock, the (first or second) alpha-olefin (e.g., carbon number and/or olefin type, among other olefin features), the (first or second) chemically-treated solid oxide, the liquid medium, and the conditions under which the (first or second) oligomer product is formed, among others) are independently described herein and these features can be combined in any combination to further describe the disclosed oligomerization processes. Moreover, additional process steps can be performed before, during, and/or after any of the steps of any of the processes disclosed herein, and can be utilized without limitation and in any combination to further describe the oligomerization processes unless stated otherwise. Further, any products produced in accordance with the first and second processes are encompassed herein, such as a hydrogenated heavy oligomer product, a first hydrogenated heavy oligomer product, and/or a second hydrogenated heavy oligomer product, produced by the first and/or second process(es).

In some aspects, the (first or second) olefin feedstock can comprise, consist essentially of, of consist of, a (first or second) $C_4$ to $C_{20}$ alpha-olefin. Moreover, the (first or second) olefin feedstock can comprise, consist essentially of, or consist of, any single carbon number alpha-olefin from $C_4$ to $C_{20}$ (e.g., a $C_{10}$ alpha-olefin) or any combination of different single carbon number alpha-olefins from $C_4$ to $C_{20}$ (e.g., $C_6$-$C_{14}$ alpha-olefins, or $C_8$-$C_{12}$ alpha-olefins, among other combinations). Olefin feedstocks and alpha-olefins are described herein and their features can be utilized without limitation to further describe the (first or second) olefin feedstocks and (first or second) alpha-olefins which can be utilized in the oligomerization processes.

In steps (a) and (A) of the first and second processes, a first olefin feedstock comprising a first $C_4$-$C_{20}$ alpha-olefin can be contacted with a first catalyst system in a first reaction zone to form a first oligomer product. In some aspects, these steps can include adding the first olefin feedstock, the first catalyst system, and additional unrecited materials (e.g., a non-olefin solvent or diluent, a stabilizer, amongst other materials) into the first reaction zone. In other aspects, these steps can consist essentially of adding the first olefin feedstock and the first catalyst system into the first reaction zone or, alternatively, consist of adding the first olefin feedstock and the first catalyst system into the first reaction zone. For instance, these oligomerization steps can be performed in the presence of a non-olefin solvent. The amount of any non-olefin solvent used in addition to the disclosed alpha-olefins of the first olefin feedstock is not limited to any particular range. Such solvent, or combination of solvents, can be used, for example, as a flow modifier to alter the flow properties or viscosity of the reaction zone mixture including the first olefin feedstock (or first alpha-olefin) and/or the first oligomer product.

Illustrative non-olefin organic solvents that can be utilized in the processes disclosed herein can include aliphatic hydrocarbons, petroleum distillates, or combinations thereof; alternatively, aliphatic hydrocarbons; or alternatively, petroleum distillates. Specific and non-limiting examples of non-olefin organic solvents that can be utilized in the processes disclosed herein can include pentane, hexane, heptane, octane, cyclohexane, methyl cyclohexane, and the like, as well as mixtures or combinations thereof. In other aspects, these steps can be performed in the substantial absence of a solvent (e.g., less than 10, 5, 4, 3, 2, or 1 wt. % solvent, based upon the total weight of the olefin feedstock and the solvent).

These steps of contacting the first olefin feedstock with the first catalyst system in the first reaction zone to form the first oligomer product can be conducted under any suitable oligomerization conditions. In an aspect, the oligomerization temperature can be a minimum temperature of 0° C., 10° C., 15° C., or 20° C., and a maximum temperature of 250° C., 225° C., 200° C., 180° C., or 150° C. Representative and non-limiting ranges for the oligomerization temperature can include from 0° C. to 250° C., from 15° C. to 225° C., from 20° C. to 180° C., from 10° C. to 150° C., from 15° C. to 70° C., from 20° C. to 85° C., or from 30° C. to 80° C., and the like. These temperature ranges also are meant to encompass circumstances where the oligomerizing step can be conducted at a series of different temperatures, instead of at a single fixed temperature, falling within the respective temperature ranges.

Generally, the oligomerization steps can be performed at any suitable pressure. While not being limited thereto, these steps can be conducted at a reactor pressure in a range from atmospheric pressure to 4,000 psig (27.6 MPag), from 1 psig (6.9 kPag) to 3,000 psig (20.9 MPag), from 5 psig (34 kPag) to 2,000 psig (13.8 MPag), or from 100 psig (689 kPag) to 1,500 psig (10.3 MPag), and the like. In one aspect, the oligomerization step is performed (and the first oligomer product is formed) in the substantial absence of hydrogen (e.g., no added hydrogen), while in another aspect, the oligomerization step is performed (and the first oligomer product is formed) in the presence of added hydrogen. Typical hydrogen partial pressures include, but are not limited to, from 1 psig (6.9 kPag) to 2000 psig (13.8 MPag), from 5 psig (34 kPag) to 1500 psig (10.3 MPag), from 10 psig (69 kPag) to 1000 psig (6.9 MPag), from 10 psig (69 kPag) to 500 psig (3.5 MPag), or from 25 psig (172 kPag) to 500 psig (3.4 MPag), and the like.

The first reaction zone can comprise any suitable reactor or vessel in order to form the first oligomer product, non-limiting examples of which can include a fixed bed reactor, a stirred tank reactor, a plug flow reactor, a loop slurry reactor, and a tubular reactor, including more than one reactor in series or in parallel, and including any combination of reactor types and arrangements. The oligomerization step disclosed herein can be a batch process in some aspects, while in other aspects, the oligomerization step can be a continuous process.

Any suitable oligomerization catalyst system can be used as the first catalyst system, such as illustrative catalyst systems that contain a Lewis acid, an acidic ionic liquid, a clay, an acidic clay or an acid washed clay, an acidic ion exchange resin, and the like, as well as combinations thereof. In some aspects, the first catalyst system can comprise any suitable metallocene-based catalyst system. In one aspect, for instance, the first catalyst system can comprise a first metallocene compound and an aluminoxane compound, while in another aspect, the first catalyst system can comprise a first metallocene compound, a first chemically-treated solid oxide, and a first organoaluminum compound. Regardless of the metallocene-based catalyst system, the first metallocene compound can be present in any suitable form, such as a solution in a solvent, or as a solid in a diluent.

In steps (b), (c), and (d) of the first process, (b) the first reaction zone effluent comprising the first oligomer product is discharged from the first reaction zone, followed by (c) optionally deactivating the first catalyst system to form a deactivated first catalyst system, and isolating an effluent fraction by removing at least a portion of the first catalyst system or the deactivated first catalyst system from the first reaction zone effluent, and then (d) isolating the first oligomer product by removing at least a portion of unreacted first $C_4$-$C_{20}$ alpha-olefin from the effluent fraction. In these steps, the first reaction zone effluent, which comprises the first oligomer product, is withdrawn from the first reaction zone, followed by isolating the effluent fraction by removal of at least a portion of the first catalyst system (whether deactivated, or not) from the first reaction zone effluent. Various suitable separations steps can be employed for this isolation step, as would be recognized by those of skill in the art. In an aspect, and not limited thereto, a filtration step can be used for removal of at least a portion of the first catalyst system (whether deactivated, or not).

Optionally, the first catalyst system can be deactivated prior to removal from the first reaction zone effluent. Deactivating the first catalyst system can comprise contacting the first reaction zone effluent with a suitable catalyst deactivating agent, or subjecting the reaction zone effluent to suitable process steps to deactivate the catalyst system, or a combination of both. The catalyst deactivating agent can comprise (or consist essentially of, or consist of) water, an alcohol compound, an amine compound, or any combination thereof; alternatively, water; alternatively, an alcohol compound; or alternatively, an amine compound. In an aspect, the alcohol compound can be a monoalcohol compound, a diol compound, a polyol compound, or any combination thereof. In some aspects, the alcohol compound can comprise, consist essentially of, or consist of, a $C_1$ to $C_{20}$ mono alcohol. In some aspects, the alcohol compound can comprise, consist essentially of, or consist of, methanol, ethanol, a propanol, a butanol, a pentanol, a hexanol, a heptanol, an octanol, a nonanol, a decanol, an undecanol, or mixtures thereof. In some aspects, the alcohol compound can comprise, consist essentially of, or consist of, methanol, ethanol, 1-propanol, 2-propanol, 1-butanol, 2-butanol, iso-butanol, sec-butanol, t-butanol, 1-hexanol, 2-hexanol, 3-hexanol, 1-heptanol, 2-heptanol, 3-heptanol, 4-heptanol, 1-octanol, 2-octanol, 3-octanol, 4-octanol, 2-ethyl-1-hexanol, 2-methyl-3-heptanol, 1-decanol, 2-decanol, 3-decanol, 4-decanol, 5-decanol, 1-undecanol, 2-undecanol, 7-methyl-2-decanol, a 1-docecanol, a 2-dodecanol, 2-ethyl-1-decanol, and mixtures thereof.

Additionally or alternatively, the first catalyst system can be deactivated by contact with an aqueous solution (e.g., an aqueous Group 1 metal hydroxide solution or an aqueous mineral acid solution). Such deactivation processes to deactivate the catalyst system can also potentially remove a portion, or substantially all, of the metal catalyst system components from the first reaction zone effluent.

From the effluent fraction, the first oligomer product can be isolated by removing at least a portion of unreacted first $C_4$-$C_{20}$ alpha-olefin from the effluent fraction. Thus, in this isolation step, unreacted alpha-olefin monomer is removed, and typically, purified and recycled for use as a portion of the first olefin feedstock, although this is not a requirement. As would be recognized by one of skill in the art, this isolation step can be performed using any suitable technique, such as a filtration process, a flash process, or a distillation process, as well as combinations of two or more of these techniques. Moreover, these techniques can be performed at atmospheric or any suitable sub-atmospheric pressure, if desired.

In steps (B), (C), and (D) of the second process, (B) the first reaction zone effluent comprising the first oligomer product is discharged from the first reaction zone, wherein the first oligomer product can comprise a first light fraction comprising $C_{26}$ and lower oligomers (e.g., $C_8$-$C_{26}$), and a first heavy oligomer product comprising $C_{28}$ and higher oligomers, followed by (C) isolating the first light fraction and isolating the first heavy oligomer product from the first oligomer product, and then (D) hydrogenating at least a portion of the first heavy oligomer product to produce a first hydrogenated heavy oligomer product. In these steps, the first reaction zone effluent, which comprises the first oligomer product, is withdrawn from the first reaction zone. The first oligomer product generally comprises a first light fraction (which comprises $C_{26}$ and lower oligomers, such as $C_8$-$C_{26}$ oligomers), and a first heavy oligomer product (which comprises $C_{28}$ and higher oligomers). In some aspects, the first light fraction can contain at least 75 wt. %, at least 80 wt. %, at least 90 wt. %, at least 95 wt. %, or at least 98 wt. %, of $C_{26}$ and lower oligomers. Thus, if the olefin feedstock is 1-octene, for instance, then the light fraction contains predominantly dimers and trimers—unreacted monomer is generally removed and recycled as the olefin feedstock. Likewise, the first heavy oligomer product can contain at least 75 wt. %, at least 80 wt. %, at least 90 wt. %, at least 95 wt. %, or at least 98 wt. %, of $C_{28}$ and higher oligomers.

From the first oligomer product, the first light fraction and the first heavy oligomer product can be isolated. As described herein, this isolation step can be performed using any suitable technique, such as a filtration process, a flash process, or a distillation process, as well as combinations of two or more of these techniques, and such techniques can be performed at atmospheric or any suitable sub-atmospheric pressure.

The resulting first heavy oligomer product, or any portion thereof, can then be hydrogenated to form a first hydrogenated heavy oligomer product. Suitable hydrogenation procedures and associated metal catalysts (e.g., platinum, rhenium, palladium, nickel, etc.) are well known to those of skill in the art. Generally, the first heavy oligomer product, or any portion thereof, can be hydrogenated to provide a first hydrogenated heavy oligomer product having the desired degree of saturation (which can be quantified as a bromine number or bromine index). The bromine number can be determined by ASTM D1159-09, while the bromine index can be determined by ASTM D2710-09. The first hydrogenated heavy oligomer product also can be referred to as a polyalphaolefin.

In the first and second processes, the first catalyst system can be periodically or continuously introduced to the first reaction zone, and the first reaction zone effluent can be periodically or continuously discharged from the first reaction zone. Likewise, in the first and second processes, the first olefin feedstock can be periodically or continuously introduced to the first reaction zone, and the first reaction zone effluent can be periodically or continuously discharged from the first reaction zone.

Referring now to steps (e) and (E) of the first and second processes, a suspension (or slurry) of a second chemically-treated solid oxide in a liquid medium, a second metallocene compound, a second organoaluminum compound, and a second olefin feedstock comprising a second $C_4$-$C_{20}$ alpha-olefin, can be contacted in a second reaction zone to form a second oligomer product. In step (e), the liquid medium can comprise at least a portion of the effluent fraction and/or at least a portion of the first oligomer product. Thus, the liquid medium can comprise at least a portion of the effluent fraction, or at least a portion of the first oligomer product, or at least a portion of the effluent fraction and at least a portion of the first oligomer product. In step (E), the liquid medium can comprise at least a portion of one or more of the first light fraction, the first heavy oligomer product, the first hydrogenated heavy oligomer product, or any combination thereof. Thus, the liquid medium can comprise at least a portion of the first light fraction, or at least a portion of the first heavy oligomer product, or at least a portion of the first hydrogenated heavy oligomer product, or at least a portion of any mixture or combination of the first light fraction, the first heavy oligomer product, and the first hydrogenated heavy oligomer product.

Similar to steps (a) and (A), steps (e) and (E) can include the contacting of additional unrecited materials (e.g., a non-olefin solvent or diluent, a stabilizer, amongst other materials) in the second reaction zone. In other aspects, these steps can consist essentially of contacting the suspension, the second metallocene compound, the second organoaluminum compound, and the second olefin feedstock in the second reaction zone or, alternatively, consist of contacting the suspension, the second metallocene compound, the second organoaluminum compound, and the second olefin feedstock in the second reaction zone. For instance, the oligomerization steps (e) and (E) can be performed in the presence of a non-olefin solvent. The amount of any non-olefin solvent used in addition to the disclosed alpha-olefins of the second olefin feedstock is not limited to any particular range. Such solvent, or combination of solvents, can be used, for example, as a flow modifier to alter the flow properties or viscosity of the reaction zone mixture including the second olefin feedstock (or second alpha-olefin) and/or the second oligomer product. Illustrative non-olefin organic solvents that can be utilized in the processes disclosed herein can include aliphatic hydrocarbons, petroleum distillates, or combinations thereof; alternatively, aliphatic hydrocarbons; or alternatively, petroleum distillates. In other aspects, these steps can be performed in the substantial absence of a solvent (e.g., less than 10, 5, 4, 3, 2, or 1 wt. % solvent, based upon the total weight of the olefin feedstock and the solvent).

The oligomerization steps (e) and (E) and the formation of the second oligomer product can be conducted under any suitable oligomerization conditions, and these conditions can generally encompass the same oligomerization temperature ranges, reactor pressures, and hydrogen partial pressures (if hydrogen is used) disclosed herein for steps (a) and (A). Thus, the first oligomer product and the second oligomer product can be formed at the same or different oligomerization conditions, and the first oligomer product and the second oligomer product can be the same or different.

The second reaction zone can be the same as or different from the first reaction zone, and can comprise any suitable reactor or vessel in order to form the second oligomer product, non-limiting examples of which can include a fixed bed reactor, a stirred tank reactor, a plug flow reactor, a loop slurry reactor, and a tubular reactor, including more than one reactor in series or in parallel, and including any combination of reactor types and arrangements. The oligomerization step disclosed herein can be a batch process in some aspects, while in other aspects, the oligomerization step can be a continuous process. As one of skill in the art would readily recognize, when the first and second processes are continuous, the first reaction zone and the second zone can be the same (i.e., the same oligomerization reactor system). Moreover, the processes disclosed herein are applicable to oligomerization processes in start-up mode and/or in "steady-state" continuous production.

In one aspect, steps (e) and (E) of the first and second processes can be performed by contacting (or mixing or combining), in any order or sequence, the suspension of the second chemically-treated solid oxide in the liquid medium, the second metallocene compound, the second organoaluminum compound, and the second olefin feedstock comprising the second $C_4$-$C_{20}$ alpha-olefin. Any of these components can be introduced (or added, charged, or fed) directly into the second reaction zone, or combined with any other component(s) prior to being introduced to the second reaction zone. For example, in step (e) and/or step (E), the suspension of the second chemically-treated solid oxide in the liquid medium, the second metallocene compound, and the second organoaluminum compound can be introduced separately to the second reaction zone. As another example, in step (e) and/or step (E), at least two of the suspension of the second chemically-treated solid oxide in the liquid medium, the second metallocene compound, and the second organoaluminum compound can be combined (for instance, in a catalyst preparation vessel) prior to being introduced to the second reaction zone. The second metallocene compound can be present in any suitable form, such as a solution in a solvent, or as a solid in a diluent.

In another aspect, step (e) and/or step (E) can comprise i) contacting the suspension of the second chemically-treated solid oxide in the liquid medium with the second organoaluminum compound for a precontact time to form a precontacted mixture (e.g., in a chemically-treated solid oxide mix tank), ii) contacting the precontacted mixture with the second metallocene compound to form a second metallocene-based catalyst system (e.g., in a catalyst preparation vessel), and iii) contacting the second metallocene-based catalyst system with the second olefin feedstock in the second reaction zone to form the second oligomer product. Optionally, step ii) can comprise contacting the precontacted mixture with the second metallocene compound and an additional organoaluminum compound, and the additional organoaluminum compound can be the same as or different from the second organoaluminum compound.

In yet another aspect, step (e) and/or step (E) can comprise i) contacting the suspension of the second chemically-treated solid oxide in the liquid medium with the second organoaluminum compound for a precontact time to form a precontacted mixture, ii) introducing the precontacted mixture and the second metallocene compound separately to the second reaction zone, and iii) contacting the precontacted mixture and the second metallocene compound with the second olefin feedstock in the second reaction zone to form the second oligomer product.

The duration of any precontacting step (e.g., the precontact time) and of any storage or aging of the suspension (e.g., storage time of the suspension prior to contacting with any of the second metallocene compound, the second organoaluminum compound, and the second olefin feedstock) in the first and second processes are not limited to any particular period of time. Likewise, assuming that the catalyst system is not intended for long term storage, which could extend for days or weeks, the second period of time is not limited to any particular period of time. The appropriate precontact time and/or storage time independently can depend upon, for example, the relative amounts of the respective catalyst system components, the temperatures at which the components are contacted or storage, the presence of other materials, and the degree of mixing, among other variables. Typically, however, the minimum precontact time and storage time, independently, can be 5 seconds, 10 seconds, 30 seconds, 1 minute, 5 minutes, 10 minutes, or 20 minutes; additionally or alternatively, the maximum precontact time and storage time, independently, can be 48 hours, 36 hours, 24 hours, 18 hours, 12 hours, 6 hours, 4 hours, or 2 hours. Generally, the precontact time and the storage time can be in a range from any minimum time disclosed herein to any maximum time disclosed herein. Accordingly, suitable non-limiting ranges for the precontact time and the storage time independently can include the following: at least 5 seconds, at least 1 minute, from 5 seconds to 48 hours, from 10 seconds to 36 hours, from 30 seconds to 24 hours, from 30 seconds to 6 hours, from 1 minute to 18 hours, from 5 minutes to 24 hours, from 5 minutes to 6 hours, from 10 minutes to 4 hours, from 10 minutes to 45 minutes, or from 20 minutes to 2 hours. Other appropriate ranges for the precontact time and the storage time are readily apparent from this disclosure.

In steps (e) and (E) of the first and second processes, the suspension can comprise (or consist essentially of, or consist of) the second chemically-treated solid oxide and the liquid medium. As disclosed, the liquid medium can comprise at least a portion of the effluent fraction, at least a portion of the first oligomer product, at least a portion of the first light fraction, at least a portion of the first heavy oligomer product, at least a portion of the first hydrogenated heavy oligomer product, or any mixture or combination of these materials. Regardless of the source of liquid medium, the 100° C. kinematic viscosity of the liquid medium typically can fall within a range from 2 to 200 cSt, with illustrative and non-limiting ranges including from 2 to 150 cSt, from 4 to 150 cSt, from 2 to 20 cSt, from 4 to 15 cSt, from 60 to 200 cSt, from 60 to 150 cSt, from 100 to 200 cSt, and the like.

Generally, the predominant component of the suspension is the liquid medium. Typical loadings of the second chemically-treated solid oxide can range from 1 to 30 wt. %, from 2 to 25 wt. %, from 2 to 20 wt. %, from 3 to 18 wt. %, from 5 to 18 wt. %, from 5 to 15 wt. %, or from 6 to 12 wt. %. These weight percentages are based on the weight of the second chemically-treated solid oxide versus the total weight of the second chemically-treated solid oxide and the liquid medium in the suspension.

Steps (f), (g), and (h) of the first process include (f) discharging a second reaction zone effluent comprising the second oligomer product from the second reaction zone, the second oligomer product comprising a light fraction comprising $C_{26}$ and lower oligomers (e.g., $C_8$-$C_{26}$), and a heavy oligomer product comprising $C_{28}$ and higher oligomers, followed by (g) isolating the heavy oligomer product from the second oligomer product, and then (h) hydrogenating at least a portion of the heavy oligomer product to produce a hydrogenated heavy oligomer product. Similarly, steps (F), (G), (H) of the second process include (F) discharging a second reaction zone effluent comprising the second oligomer product from the second reaction zone, the second oligomer product comprising a second light fraction comprising $C_{26}$ and lower oligomers (e.g., $C_8$-$C_{26}$), and a second heavy oligomer product comprising $C_{28}$ and higher oligomers, followed by (G) isolating the second heavy oligomer product from the second oligomer product, and then (H) hydrogenating at least a portion the second heavy oligomer product to produce a second hydrogenated heavy oligomer product. In these steps, the second reaction zone effluent, which comprises the second oligomer product, is withdrawn from the second reaction zone. The second oligomer product generally comprises a light (or second light) fraction (which comprises $C_{26}$ and lower oligomers, such as $C_8$-$C_{26}$ oligomers), and a heavy (or second heavy) oligomer product (which comprises $C_{28}$ and higher oligomers).

Similar to the first catalyst system, the second catalyst system can be deactivated prior to its removal from the second reaction zone effluent. Deactivating the second catalyst system can comprise contacting the second reaction zone effluent with a suitable catalyst deactivating agent, or subjecting the second reaction zone effluent to suitable process steps to deactivate the catalyst system, or a combination of both, as described herein.

From the second oligomer product, the heavy (or second heavy) oligomer product can be isolated. As described herein, this isolation step can be performed using any suitable technique, such as a filtration process, a flash process, or a distillation process, as well as combinations of two or more of these techniques, and such techniques can be performed at atmospheric or any suitable sub-atmospheric pressure.

The resulting heavy (or second heavy) oligomer product, or any portion thereof, can then be hydrogenated to form a hydrogenated heavy (or second hydrogenated heavy) oligomer product. Suitable hydrogenation procedures and associated metal catalysts (e.g., platinum, rhenium, palladium, nickel, etc.) are well known to those of skill in the art. Generally, the first heavy (or second heavy) oligomer product, or any portion thereof, can be hydrogenated to provide a hydrogenated heavy (or second hydrogenated heavy) oligomer product having the desired degree of saturation (which can be quantified as a bromine number or bromine index). The bromine number can be determined by ASTM D1159-09, while the bromine index can be determined by ASTM D2710-09. The hydrogenated heavy (or second hydrogenated heavy) oligomer product also can be referred to as a polyalphaolefin.

In the first and second processes, the hydrogenated heavy oligomer product, the first hydrogenated heavy oligomer product, and the second hydrogenated heavy oligomer product can be the same or different and, independently, can comprise less than 0.5 wt. % hydrogenated monomer, less than 5 wt. % hydrogenated $C_{26}$ and lower oligomers, and at least 80 wt. % hydrogenated $C_{28}$ and higher oligomers. In a further aspect, the hydrogenated heavy oligomer product, the first hydrogenated heavy oligomer product, and the second hydrogenated heavy oligomer product can be the same or different and, independently, can comprise less than 0.2 wt. % hydrogenated monomer, less than 1 wt. % hydrogenated $C_{26}$ and lower oligomers, and at least 90 wt. % hydrogenated $C_{28}$ and higher oligomers.

In the first and second processes, the first catalyst system can be periodically or continuously introduced to the first reaction zone, and the first reaction zone effluent can be periodically or continuously discharged from the first reaction zone. Likewise, in the first and second processes, the first olefin feedstock can be periodically or continuously introduced to the first reaction zone, and the first reaction zone effluent can be periodically or continuously discharged from the first reaction zone.

Additionally, in the first and second processes, the suspension of the second chemically-treated solid oxide, the second metallocene compound, and the second organoaluminum compound, independently, can be periodically or continuously introduced to the second reaction zone, and the second reaction zone effluent can be periodically or continuously discharged from the second reaction zone. Likewise, in the first and second processes, the second olefin feedstock can be periodically or continuously introduced to the second reaction zone, and the second reaction zone effluent can be periodically or continuously discharged from the second reaction zone.

Consistent with aspects of this invention, the first catalyst system and the second metallocene-based catalyst system can be the same or different. Further, the first catalyst system and the second metallocene-based catalyst system, independently, can be substantially free of aluminoxane compounds, organoboron or organoborate compounds, ionizing ionic compounds, or any combination thereof, in some aspects. Herein, substantially free of aluminoxane compounds, organoboron or organoborate compounds, and/or ionizing ionic compounds, means that the respective catalyst system contains less than 5 wt. %, 2.5 wt. %, 1 wt. %, 0.5 wt. %, 0.25 wt. %, or 0.1 wt. % of aluminoxane compounds, organoboron or organoborate compounds, and/or ionizing ionic compounds, based upon the total amount of organoaluminum compound in the catalyst system. Thus, the first catalyst system and the second metallocene-based catalyst system can have significant catalyst activity without such materials. For instance, the (first or second) catalyst system can consist essentially of a (first or second) chemically treated solid oxide, a (first or second) metallocene compound, and a (first or second) organoaluminum compound, wherein no other materials are present in the (first or second) catalyst system which would increase/decrease the activity or productivity of the catalyst system by more than about 10% from the catalyst activity or productivity of the catalyst system in the absence of said materials (e.g., aluminoxane materials).

Generally, in the (first or second) catalyst systems, the weight ratio of the (first or second) chemically-treated solid oxide to the (first or second) metallocene compound can be in a range from 10:1 to 5000:1, for instance, from 20:1 to 1500:1, from 50:1 to 1500:1, from 50:1 to 1000:1, from 50:1 to 800:1, from 60:1 to 800:1, from 60:1 to 600:1, from 70:1 to 600:1, or from 70:1 to 500:1, and the like. Other appropriate weight ratios are readily apparent from this disclosure. Further, if more than one metallocene compound and/or more than one chemically-treated solid oxide are employed, this ratio is based on the total weight of each respective component.

Likewise, the molar ratio of aluminum of the (first or second) organoaluminum compound to transition metal of the (first or second) metallocene compound can be in a range from 2:1 to 7000:1, for instance, from 5:1 to 5000:1, from 5:1 to 1000:1, from 5:1 to 250:1, or from 10:1 to 150:1, and the like. Other appropriate molar ratios are readily apparent from this disclosure. Further, if more than one organoaluminum compound and/or more than one metallocene compound are employed, this ratio is based on the total amount of each respective component.

In the (first or second) oligomerization process, the molar ratio of the alpha-olefins to the metallocene compound is not particularly limited. In some aspects, however, the molar ratio of alpha-olefins of the (first or second) olefin feedstock to the (first or second) metallocene compound can be in a range from $1\times10^3$:1 to $1\times10^9$:1; alternatively, from $1\times10^4$:1 to $1\times10^8$:1; alternatively, from $1\times10^5$:1 to $1\times10^7$:1; or alternatively, from $1\times10^5$:1 to $1\times10^6$:1. Other appropriate molar ratios of the alpha-olefins to the metallocene compound are readily apparent from this disclosure.

In accordance with the processes of this invention, the activity of the (first or second) catalyst system under oligomerization conditions generally can be at least 5,000 grams, at least 10,000 grams, at least 20,000 grams, at least 25,000 grams, or at least 50,000 grams, and often up to 75,000-150,000 grams, of (first or second) oligomer product per gram of (first or second) metallocene compound per hour. For the purpose of determining the activity, the conditions under which the oligomer product is formed can include a triisobutylaluminum co-catalyst, using neat 1-octene as the olefin feedstock and 10 psig hydrogen pressure, and with an oligomerization temperature of 110° C.

Olefin Feedstocks

A wide range of olefin feedstocks comprising, consisting essentially of, or consisting of, $C_4$-$C_{20}$ alpha-olefins can be oligomerized according to the processes provided herein. Further, the alpha-olefins can comprise, or consist essentially of, normal alpha-olefins. Generally, the first olefin feedstock and the second olefin feedstock are the same or different and independently can comprise (or consist essentially of, or consist of) a $C_4$-$C_{20}$ alpha-olefin, and this includes any mixture or combination thereof. Thus, a mixture of alpha-olefins having different numbers of carbon atoms can be used, or alpha-olefins having predominantly a single number of carbon atoms can be used as the olefin feedstock.

In one aspect, the first olefin feedstock and the second olefin feedstock are the same or different and independently can comprise (or consist essentially of, or consist of) a $C_4$-$C_{20}$ alpha-olefin (or normal alpha-olefin) or a $C_6$-$C_{18}$ alpha-olefin (or normal alpha-olefin). In another aspect, the first olefin feedstock and the second olefin feedstock are the same or different and independently can comprise (or consist essentially of, or consist of) a $C_6$-$C_{14}$ alpha-olefin (or normal alpha-olefin). In yet another aspect, the first olefin feedstock and the second olefin feedstock are the same or different and independently can comprise (or consist essentially of, or consist of) a $C_8$-$C_{12}$ alpha-olefin (or normal alpha-olefin).

The first olefin feedstock and the second olefin feedstock, in particular aspects of this invention, are the same or different and independently can comprise (or consist essentially of, or consist of) 1-hexene, 1-octene, 1-decene, 1-dodecene, 1-tetradecene, 1-hexadecene, or any combination thereof; alternatively, 1-octene, 1-decene, 1-dodecene, or any combination thereof; alternatively, 1-hexene; alternatively, 1-octene; alternatively, 1-decene, alternatively, 1-dodecene; alternatively, 1-tetradecene; or alternatively, 1-hexadecene. Thus, mixtures of alpha-olefins (or normal alpha-olefins) having different numbers of carbon atoms can be used, or alpha-olefins (or normal alpha-olefins) having predominantly a single number of carbon atoms can be used as the first olefin feedstock and/or the second olefin feedstock.

In an aspect, the first olefin feedstock and the second olefin feedstock are the same or different and independently comprise any suitable amount of the $C_4$-$C_{20}$ alpha-olefin (or normal alpha-olefin). For example, the first olefin feedstock and the second olefin feedstock independently can contain at least 50 wt. %, at least 70 wt. %, at least 80 wt. %, at least 90 wt. %, or at least 95 wt. %, of $C_4$-$C_{20}$ alpha-olefin(s) (or normal alpha-olefin(s)). Illustrative ranges for the amount of $C_4$-$C_{20}$ alpha-olefin(s) (or normal alpha-olefin(s)) in the first olefin feedstock and the second olefin feedstock, independently, can include from 50 to 100 wt. %, from 55 to 99 wt. %, from 60 to 98 wt. %, from 65 to 97 wt. %, from 70 to 96 wt. %, from 75 to 100 wt. %, from 80 to 100 wt. %, or from 80 to 98 wt. %, of $C_4$-$C_{20}$ alpha-olefin(s) (or normal alpha-olefin(s)). Other weight percent ranges are readily apparent from this disclosure.

In sum, the first olefin feedstock and the second olefin feedstock are the same or different and independently can contain any suitable amount of any olefin, olefin carbon number range, or mixture of olefins described herein. For instance, the first olefin feedstock and the second olefin feedstock independently can contain from 50 to 100 wt. %, from 55 to 99 wt. %, from 60 to 98 wt. %, from 65 to 97 wt. %, from 70 to 96 wt. %, from 75 to 100 wt. %, from 80 to 100 wt. %, or from 80 to 98 wt. % $C_4$-$C_{20}$ alpha-olefins (or normal alpha-olefins); alternatively, alpha-olefins (or normal alpha-olefins) of any carbon number range described herein;

alternatively, of any combination of single carbon numbered alpha-olefins (or normal alpha-olefins) described herein; or alternatively, of any single carbon numbered alpha-olefins (or normal alpha-olefins) described herein. For instance, in a non-limiting example, the first olefin feedstock and the second olefin feedstock independently can comprise at least 75 wt. %, at least 80 wt. %, at least 85 wt. %, at least 90 wt. %, or at least 95 wt. %, of 1-hexene; alternatively, 1-octene; alternatively, 1-decene; alternatively, 1-dodecene; alternatively, 1-tetradecene; or alternatively, 1-hexadecene.

As described herein, the first olefin feedstock and the second olefin feedstock independently can comprise various carbon number ranges and/or types of olefins. The various carbon numbers of the olefin(s), the type of olefin(s), and the weight percentage of the olefin(s) can be combined in any fashion to describe the first olefin feedstock and the second olefin feedstock that can be used in the oligomerization processes of this invention.

Metallocene Compounds

The oligomerization processes and catalyst systems disclosed herein can employ a first metallocene compound and a second metallocene compound, and the first metallocene compound and the second metallocene compound can be the same or different, and independently can comprise any suitable metallocene compound, for example, that can be used to oligomerize an olefin.

In some aspects, the first metallocene compound, or the second metallocene compound, or both the first metallocene compound and the second metallocene compound, can comprise a bridged metallocene compound. In one aspect, for instance, the first metallocene compound and the second metallocene compound are the same or different and independently can comprise a bridged zirconium or hafnium based metallocene compound. In another aspect, the first metallocene compound and the second metallocene compound are the same or different and independently can comprise a bridged zirconium based metallocene with a cyclopentadienyl group and a carbon bridging atom or a silicon bridging atom. In yet another aspect, the first metallocene compound and the second metallocene compound are the same or different and independently can comprise a single atom bridged, zirconium or hafnium based metallocene compound containing two cyclopentadienyl groups. In still another aspect, the first metallocene compound and the second metallocene compound are the same or different and independently can comprise a bridged zirconium based metallocene compound containing two cyclopentadienyl groups with a carbon bridging atom or a silicon bridging atom.

In some aspects, the first metallocene compound, or the second metallocene compound, or both the first metallocene compound and the second metallocene compound, can comprise a unbridged metallocene compound. For instance, the first metallocene compound and the second metallocene compound are the same or different and independently can comprise an unbridged zirconium or hafnium based metallocene compound containing two cyclopentadienyl groups, two indenyl groups, or a cyclopentadienyl group and an indenyl group; alternatively, an unbridged zirconium or hafnium based metallocene compound containing two cyclopentadienyl groups; alternatively, an unbridged zirconium based metallocene compound containing two cyclopentadienyl groups; alternatively, an unbridged zirconium based metallocene compound containing two alkyl-substituted cyclopentadienyl groups; alternatively, an unbridged zirconium or hafnium based metallocene compound containing two indenyl groups; alternatively, an unbridged zirconium based metallocene compound containing two indenyl groups; alternatively, an unbridged zirconium or hafnium based metallocene compound containing a cyclopentadienyl and an indenyl group; alternatively, an unbridged zirconium based metallocene compound containing a cyclopentadienyl group and an indenyl group; or alternatively, an unbridged zirconium based metallocene compound containing a cyclopentadienyl group and an indenyl group with an alkenyl substituent.

Illustrative and non-limiting examples of unbridged metallocene compounds suitable for use as the first metallocene compound and/or the second metallocene compound can have the following three representative unbridged metallocene formulas:

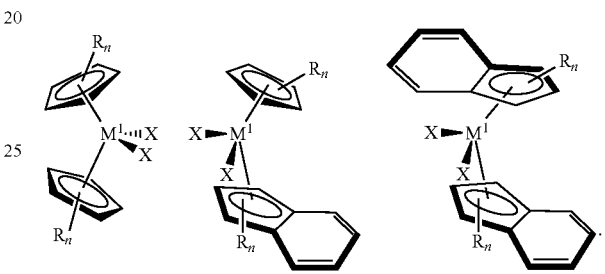

In these formulas, $M^1$ can be Zr or Hf (e.g., Zr), each X independently can be any suitable monoanionic ligand disclosed herein (e.g., a hydrocarbyl group or a halide), each R independently can be any suitable substituent (e.g., a hydrocarbyl group, a $C_1$ to $C_8$ alkyl group, or a $C_3$ to $C_8$ terminal alkenyl group), and each n independently can be any integer that conforms to the rules of chemical valence (e.g., n can be equal to 0 (unsubstituted) or n can be equal to 1 (monosubstituted)).

Specific and non-limiting examples of unbridged and bridged metallocene compounds suitable for use as the first metallocene compound and/or the second metallocene compound can include the following compounds (Ph=phenyl; Me=methyl; Ar=phenyl, substituted phenyl, or benzyl):

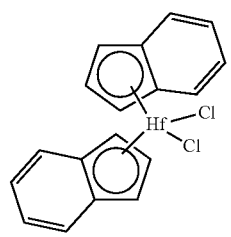

(1)

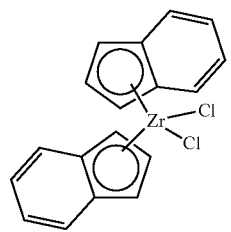

(2)

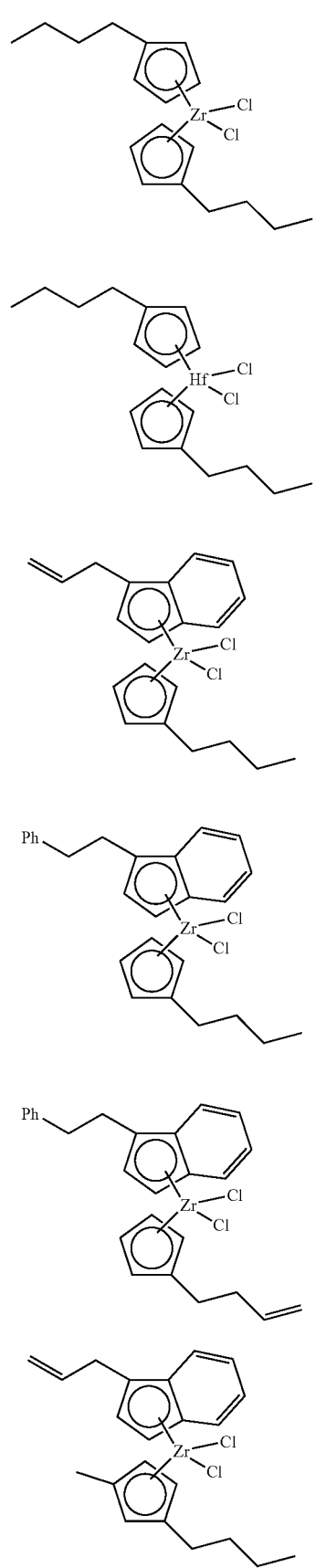
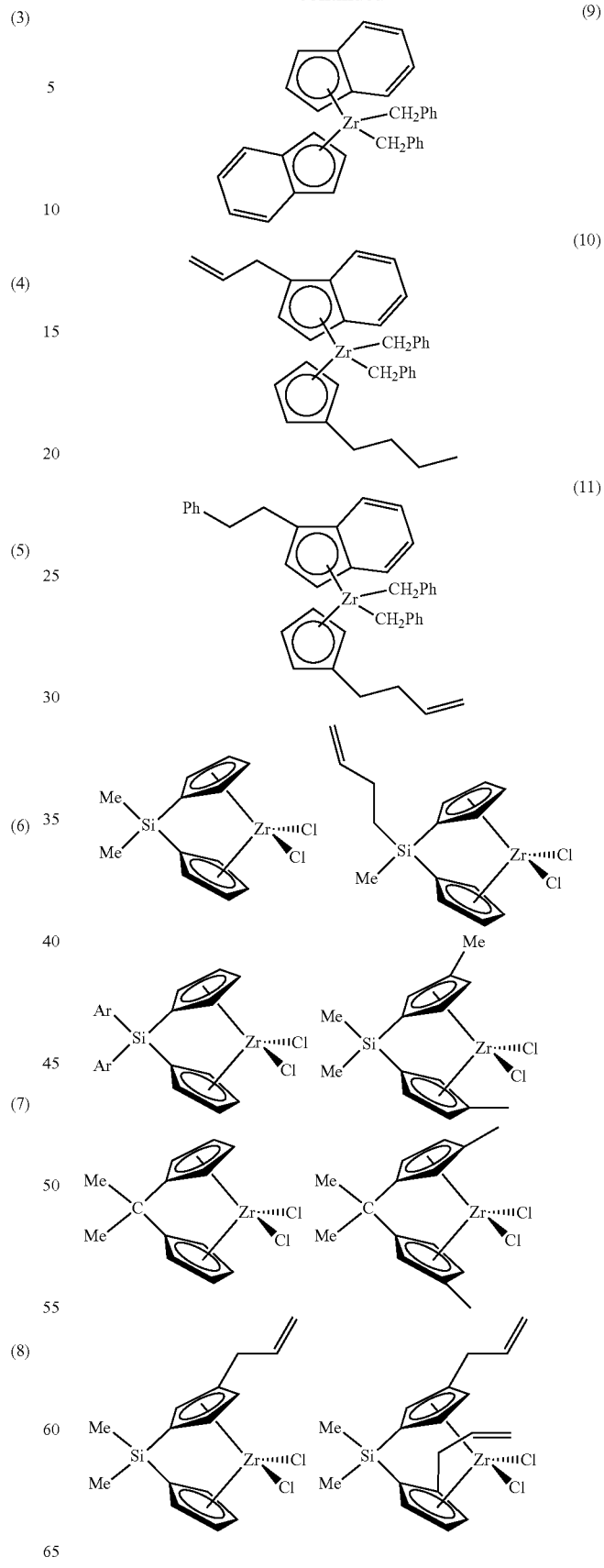
and the like, as well as combinations thereof.

The first metallocene compound and the second metallocene compound are not limited solely to the metallocene compounds such as described above. Other suitable metallocene compounds are disclosed in U.S. Pat. Nos. 7,026,494, 7,041,617, 7,199,073, 7,226,886, 7,312,283, 7,517,939, and 7,619,047, which are incorporated herein by reference in their entirety.

Chemically-Treated Solid Oxides

In the catalyst systems and oligomerization processes disclosed herein, any suitable chemically-treated solid oxide can be employed, whether one chemically-treated solid oxide or a mixture or combination of two or more different chemically-treated solid oxides. In one aspect, the first chemically-treated solid oxide and the second chemically-treated solid oxide are the same or different and independently can comprise a solid oxide treated with an electron-withdrawing anion. Alternatively, in another aspect, the first chemically-treated solid oxide and the second chemically-treated solid oxide are the same or different and independently can comprise a solid oxide treated with an electron-withdrawing anion, the solid oxide containing a Lewis-acidic metal ion. Non-limiting examples of chemically-treated solid oxides suitable for use as the first chemically-treated solid oxide and/or the second chemically-treated solid oxide are disclosed in, for instance, U.S. Pat. Nos. 7,294,599, 7,601,665, 7,884,163, 8,309,485, 8,623,973, 8,703,886, and 9,023,959, which are incorporated herein by reference in their entirety.

The solid oxide can encompass oxide materials such as alumina, "mixed oxides" thereof such as silica-alumina, coatings of one oxide on another, and combinations and mixtures thereof. The mixed oxides such as silica-alumina can be single or multiple chemical phases with more than one metal combined with oxygen to form the solid oxide. Examples of mixed oxides that can be used to form a chemically-treated solid oxide, either singly or in combination, can include, but are not limited to, silica-alumina, silica-titania, silica-zirconia, alumina-titania, alumina-zirconia, zinc-aluminate, alumina-boria, silica-boria, aluminophosphate-silica, and titania-zirconia. The solid oxide used herein also can encompass oxide materials such as silica-coated alumina, as described in U.S. Pat. No. 7,884,163 (e.g., Sasol Siral® 28, Sasol Siral® 40, etc.).

Accordingly, in one aspect, the solid oxide in the first chemically-treated solid oxide and the second chemically-treated solid oxide independently can comprise silica, alumina, silica-alumina, silica-coated alumina, aluminum phosphate, aluminophosphate, heteropolytungstate, titania, silica-titania, zirconia, silica-zirconia, magnesia, boria, zinc oxide, any mixed oxide thereof, or any combination thereof. In another aspect, the first chemically-treated solid oxide and the second chemically-treated solid oxide independently can comprise a solid oxide comprising alumina, silica-alumina, silica-coated alumina, aluminum phosphate, aluminophosphate, heteropolytungstate, titania, silica-titania, zirconia, silica-zirconia, magnesia, boria, or zinc oxide, as well as any mixed oxide thereof, or any mixture thereof. In another aspect, the first chemically-treated solid oxide and the second chemically-treated solid oxide independently can comprise a solid oxide comprising silica, alumina, titania, zirconia, magnesia, boria, zinc oxide, any mixed oxide thereof, or any combination thereof. In yet another aspect, the first chemically-treated solid oxide and the second chemically-treated solid oxide independently can comprise a solid oxide comprising silica-alumina, silica-coated alumina, silica-titania, silica-zirconia, alumina-boria, or any combination thereof. In still another aspect, the first chemically-treated solid oxide and the second chemically-treated solid oxide independently can comprise a solid oxide comprising silica, alumina, silica-alumina, silica-coated alumina, or any mixture thereof; alternatively, silica; alternatively, alumina; alternatively, silica-alumina; or alternatively, silica-coated alumina.

The silica-alumina or silica-coated alumina solid oxide materials which can be used can have a silica content from 5 to 95% by weight. In one aspect, the silica content of these solid oxides can be from 10 to 80%, or from 20% to 70%, silica by weight. In another aspect, such materials can have silica contents ranging from 15% to 60%, from 25% to 50%, from 25% to 48%, or from 20% to 45%, silica by weight. The solid oxides contemplated herein can have any suitable surface area, pore volume, and particle size, as would be recognized by those of skill in the art.

The electron-withdrawing component used to treat the solid oxide can be any component that increases the Lewis or Brønsted acidity of the solid oxide upon treatment (as compared to the solid oxide that is not treated with at least one electron-withdrawing anion). According to one aspect, the electron-withdrawing component can be an electron-withdrawing anion derived from a salt, an acid, or other compound, such as a volatile organic compound, that serves as a source or precursor for that anion. Examples of electron-withdrawing anions can include, but are not limited to, sulfate, bisulfate, fluoride, chloride, bromide, iodide, fluorosulfate, fluoroborate, phosphate, fluorophosphate, trifluoroacetate, triflate, fluorozirconate, fluorotitanate, phosphotungstate, tungstate, and molybdate, including mixtures and combinations thereof. In addition, other ionic or non-ionic compounds that serve as sources for these electron-withdrawing anions also can be employed. It is contemplated that the electron-withdrawing anion can be, or can comprise, fluoride, chloride, bromide, phosphate, triflate, bisulfate, or sulfate, or any combination thereof, in some aspects provided herein. In other aspects, the electron-withdrawing anion can comprise sulfate, bisulfate, fluoride, chloride, bromide, iodide, fluorosulfate, fluoroborate, phosphate, fluorophosphate, trifluoroacetate, triflate, fluorozirconate, fluorotitanate, or combinations thereof. Yet, in other aspects, the electron-withdrawing anion can comprise sulfate, fluoride, chloride, or combinations thereof; alternatively, sulfate; alternatively, fluoride and chloride; or alternatively, fluoride.

The (first or second) chemically treated solid oxide generally can contain from 1 to 25 wt. % of the electron-withdrawing anion, based on the weight of the (first or second) chemically-treated solid oxide. In particular aspects provided herein, the (first or second) chemically treated solid oxide can contain from 1 to 20 wt. %, from 2 to 20 wt. %, from 3 to 20 wt. %, from 2 to 15 wt. %, from 3 to 15 wt. %, from 3 to 12 wt. %, or from 4 to 10 wt. %, of the electron-withdrawing anion, based on the total weight of the (first or second) chemically-treated solid oxide.

In an aspect, the first chemically-treated solid oxide and the second chemically-treated solid oxide are the same or different and independently can comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, or phosphated silica-coated alumina, as well as any mixture or combination thereof. In another aspect, the first chemically-treated solid oxide and the second chemically-treated solid oxide are the same or different and independently can comprise a fluorided solid oxide and/or a sulfated solid oxide, non-limiting examples of which can include fluorided alumina, sulfated alumina, fluorided silica-alumina, sulfated silica-alumina, fluorided silica-zirconia, fluorided silica-coated alumina, fluorided-chlorided silica-coated alumina, or sulfated silica-coated alumina, as well as combinations thereof. In yet another aspect, the first chemically-treated solid oxide and the second chemically-treated solid oxide can comprise fluorided alumina; alternatively, chlorided alumina; alternatively, sulfated alumina; alternatively, fluorided silica-alumina; alternatively, sulfated silica-alumina; alternatively, fluorided silica-zirconia; alternatively, chlorided silica-zirconia; alternatively, sulfated silica-coated alumina; alternatively, fluorided-chlorided silica-coated alumina; or alternatively, fluorided silica-coated alumina. In some aspects, the first chemically-treated solid oxide and the second chemically-treated solid oxide are the same or different and independently can comprise a fluorided solid oxide, while in other aspects, the first chemically-treated solid oxide and the second chemically-treated solid oxide are the same or different and independently can comprise a sulfated solid oxide.

Various processes can be used to form chemically-treated solid oxides useful in the present invention. Methods of contacting the solid oxide with the electron-withdrawing component, suitable electron withdrawing components and addition amounts, impregnation with metals or metal ions (e.g., zinc, nickel, vanadium, titanium, silver, copper, gallium, tin, tungsten, molybdenum, zirconium, or combinations thereof), and various calcining procedures and conditions are disclosed in, for example, U.S. Pat. Nos. 6,107,230, 6,165,929, 6,294,494, 6,300,271, 6,316,553, 6,355,594, 6,376,415, 6,388,017, 6,391,816, 6,395,666, 6,524,987, 6,548,441, 6,548,442, 6,576,583, 6,613,712, 6,632,894, 6,667,274, 6,750,302, 7,294,599, 7,601,665, 7,884,163, and 8,309,485. Other suitable processes and procedures for preparing chemically-treated solid oxides (e.g., fluorided solid oxides, sulfated solid oxides, etc.) are well known to those of skill in the art.

Organoaluminum Compounds

The oligomerization processes and catalyst systems disclosed herein can employ a first organoaluminum compound, a second organoaluminum compound, and an additional organoaluminum compound, and the first organoaluminum compound, the second organoaluminum compound, and the additional organoaluminum compound can be the same or a different organoaluminum compound. Independently, the first organoaluminum compound, the second organoaluminum compound, and the additional organoaluminum compound can comprise any suitable organoaluminum compound, or a mixture or combination of two or more different organoaluminum compounds.

Representative and non-limiting examples of suitable organoaluminum compounds can include can include trimethylaluminum (TMA), triethylaluminum (TEA), tri-n-propylaluminum (TNPA), tri-n-butylaluminum (TNBA), tri-isobutylaluminum (TIBA), tri-n-hexylaluminum, tri-n-octylaluminum, diisobutylaluminum hydride, diethylaluminum ethoxide, diethylaluminum chloride, and the like, as well as any combination thereof. In one aspect, for instance, the first organoaluminum compound, the second organoaluminum compound, and the additional organoaluminum compound are the same or different and independently can comprise a trialkylaluminum compound, while in another aspect, the first organoaluminum compound, the second organoaluminum compound, and the additional organoaluminum compound are the same or different and independently can comprise trimethylaluminum, triethylaluminum, triisobutylaluminum, or any combination thereof alternatively, trimethylaluminum; alternatively, triethylaluminum; or alternatively, triisobutylaluminum.

Suspension Compositions

Aspects of the present invention also are directed to suspension compositions (also referred to as slurry compositions). For instance, a suspension composition of this invention can comprise (or consist essentially of, or consist of) a $C_4$-$C_{20}$ alpha-olefin oligomer product (a product produced via the oligomerization of a $C_4$-$C_{20}$ alpha-olefin) and from 1 to 30 wt. % of a chemically-treated solid oxide. The amount of the chemically-treated solid oxide in the suspension can range, for example, from 2 to 25 wt. %, from 2 to 20 wt. %, from 3 to 18 wt. %, from 5 to 18 wt. %, from 5 to 15 wt. %, or from 6 to 12 wt. %. These weight percentages are based on the total weight of the composition.

In one aspect, the suspension composition can further comprise an organoaluminum compound. Additionally or alternatively, the suspension composition can be substantially free of a metallocene compound, i.e., less than 150 ppm of the metallocene compound, based on the weight of the chemically-treated solid oxide. In some instances, the amount of the metallocene compound can be less than 100 ppm, less than 75 ppm, less than 50 ppm, less than 25 ppm, or less than 10 ppm, based on the weight of the chemically-treated solid oxide.

Generally, the viscosity of the alpha-olefin oligomer product is not limited to any particular range. Nonetheless, the 100° C. kinematic viscosity of the alpha-olefin oligomer product often can fall within a range from 2 to 200 cSt, from 2 to 150 cSt, from 2 to 12 cSt, from 4 to 150 cSt, from 4 to 15 cSt, or from 60 to 150 cSt, and the like. Other appropriate ranges for the kinematic viscosity at 100° C. of the alpha-olefin oligomer product are readily apparent from this disclosure. Kinematic viscosities at 100° C. are measured in accordance with ASTM D7042-04 (Stabinger Method).

In an aspect, the alpha-olefin oligomer product can comprise at least 80 wt. %, at least 90 wt. %, or at least 95 wt. %, of a light fraction comprising $C_{26}$ and lower oligomers, generally $C_8$-$C_{26}$ oligomers. In another aspect, the alpha-olefin oligomer product can comprise at least 80 wt. %, at least 90 wt. %, or at least 95 wt. %, of a heavy oligomer product comprising $C_{28}$ and higher oligomers. In yet another aspect, the alpha-olefin oligomer product can comprise at least 80 wt. %, at least 90 wt. %, or at least 95 wt. %, of a hydrogenated heavy oligomer product comprising hydrogenated $C_{28}$ and higher oligomers.

The alpha-olefin oligomer product can comprise, in some aspects, at least 80 wt. %, at least 90 wt. %, or at least 95 wt. %, of an effluent fraction comprising $C_4$-$C_{20}$ alpha-olefin monomer, a light fraction comprising $C_{26}$ and lower oligomers (e.g., $C_8$-$C_{26}$ oligomers), and a heavy oligomer product comprising $C_{28}$ and higher oligomers. While not being limited thereto, the effluent fraction can comprise from 10 to 30 wt. % alpha-olefin monomer and from 70 to 90 wt. % total of the light fraction and the heavy oligomer product.

In other aspects, the alpha-olefin oligomer product can comprise at least 80 wt. %, at least 90 wt. %, or at least 95 wt. %, of an oligomer product comprising a light fraction comprising $C_{26}$ and lower oligomers (e.g., $C_8$-$C_{26}$ oligomers), and a heavy oligomer product comprising $C_{28}$ and higher oligomers. In circumstances where the oligomer product has a relatively low viscosity (e.g., a 100° C. kinematic viscosity of less than 10, or less than 6 cSt), the oligomer product can contain from 50 to 85 wt. % of the light fraction and from 15 to 50 wt. % of the heavy oligomer product. In circumstances where the oligomer product has a relatively high viscosity (e.g., a 100° C. kinematic viscosity of greater than 25, greater than 60, or greater than 100 cSt), the oligomer product can contain from 2 to 15 wt. % of the light fraction and from 85 to 98 wt. % of the heavy oligomer product.

EXAMPLES

The invention is further illustrated by the following examples, which are not to be construed in any way as imposing limitations to the scope of this invention. Various other aspects, modifications, and equivalents thereof which, after reading the description herein, may suggest themselves to one of ordinary skill in the art without departing from the spirit of the present invention or the scope of the appended claims.

The chemically-treated solid oxides were prepared as follows. For sulfated alumina, Alumina A from W. R. Grace, having a surface area of about 300 m²/g and a pore volume of about 1.2 mL/g, was used. After calcining in a muffle furnace for 12 hours at 600° C., the alumina was allowed to cool. Then, the calcined alumina was impregnated with a solution of sulfuric acid in methanol, such that 3 mL of methanol were added per gram of alumina. The methanol contained enough sulfuric acid to equal about 15% sulfate based on the weight of the sulfated alumina. This sulfate-impregnated alumina was then placed in a flat pan and allowed to dry under vacuum at approximately 110° C. for about 16 hours. To calcine the support, about 10 g of the powdered mixture were placed in a 1.75-inch quartz tube fitted with a sintered quartz disk at the bottom. While the powder was supported on the disk, dry air (dried by passing through a 13× molecular sieve column) was blown upward through the disk at a rate of about 1.6 to 1.8 standard cubic feet per hour; dry nitrogen can be substituted for dry air. An electric furnace around the quartz tube was then turned on and the temperature was raised at the rate of about 400° C. per hour to the desired calcining temperature of about 600° C. (except Examples 6-9, which used different calcining temperatures). At this calcining temperature, the powder was allowed to fluidize for about three hours in the dry air. Afterward, the sulfated alumina ("SA") was collected and stored under dry nitrogen, and was used without exposure to the atmosphere.

Silica-coated aluminas were prepared as follows. The same alumina (Alumina A) used in preparing sulfated alumina was first calcined at about 600° C. for approximately 6 hours, cooled to ambient temperature, and then contacted with tetraethylorthosilicate in isopropanol to equal 25 wt. % $SiO_2$. After drying, the silica-coated alumina was calcined at 600° C. for 3 hours. Fluorided silica-coated alumina (7 wt. % F) was prepared by impregnating the calcined silica-coated alumina with an ammonium bifluoride solution in methanol, drying, and then calcining for 3 hours at 600° C. in dry air. Afterward, the fluorided silica-coated alumina ("FSCA") was collected and stored under dry nitrogen, and was used without exposure to the atmosphere.

Example 1

A feed stream of 1-octene was oligomerized in the presence of hydrogen for 1 hour at 110° C. using a catalyst system containing unbridged bis(indenyl)zirconium dichloride (27 mg), FSCA (4 g), and triisobutylaluminum (5 mL of 1M TIBA). The reaction product was filtered through dried silica gel to produce an effluent fraction, which had a 100° C. kinematic viscosity of less than 10 cSt.

A 36 g portion of the effluent fraction was mixed with 4 g of FSCA and the slurry (containing 10 wt. % FSCA) was stirred for 2 hours. The aged slurry, 27 mg of bis(indenyl)zirconium dichloride, and 5 mL of a 1 M TIBA solution in heptane were added to 1300 g of fresh 1-octene in a 1-gallon reactor. The reactor contents were heated to 110° C. and hydrogen (505 mg) was added in 4 portions over 1 hour. The reactor contents were cooled, filtered through silica gel, and distilled at 85° C. and ~20 torr to remove unreacted monomer, resulting in 554 g of an oligomer product.

Examples 2-5

A reaction product was prepared from a mixed alpha olefin feed stream using a substituted unbridged bis(indenyl) zirconium dichloride, FSCA, and triisobutylaluminum (TIBA) catalyst system. After catalyst removal, the effluent fraction olefin end groups and molecular weight distribution were determined by $^1$H NMR and are summarized as Example 2 in Table 1. The effluent fraction had a 100° C. kinematic viscosity of less than 5 cSt.

Samples of the effluent fraction of Example 2 then were mixed with FSCA in the presence or absence of varying amounts of triisobutylaluminum (1 M solution in heptane) at 33° C. After 84 hours, the slurry samples were filtered and analyzed by $^1$H NMR. Olefin end group and $^1$H NMR determined molecular weight distributions of the aged slurries of Examples 3-5 are summarized in Table 1.

In the absence of TIBA (Example 3), disappearance of vinyl and vinylidene signals was observed in the $^1$H NMR. Additionally, the integrals of the internal olefin signals and trisubstituted olefin signals were observed to increase. Finally, the calculated number-average molecular weight (Mn, g/mol) of the effluent fraction increased significantly. These results indicate that both olefin isomerization and oligomerization occurred when the effluent fraction was combined with FSCA.

In the presence of TIBA (Examples 4-5), olefin isomerization and oligomerization were suppressed. At elevated TIBA concentration (Example 5), olefin isomerization and oligomerization were completely inhibited (e.g., no change in Mn).

Thus, a potential benefit to the use of any of the liquid mediums disclosed herein as the carrier or suspending agent for a chemically-treated solid oxide, when in the presence of an organoaluminum compound, is the long-term storage stability of the mixture, which can be fed as needed to a catalyst preparation vessel and/or an oligomerization reaction zone. Another potential benefit to the use of any of the liquid mediums disclosed herein (e.g., effluent fraction, oligomer product, light fraction, etc.) as the carrier or suspending agent for a chemically-treated solid oxide is the oligomerization reaction of olefinic moieties that can occur upon contact with the chemically-treated solid oxide during storage (in the absence of the organoaluminum compound), effectively converting a portion of lighter materials, which might otherwise be discarded, into heavier oligomers that can be used for producing PAO's.

TABLE 1

| Example | FSCA (g) | Effluent (g) | TIBA (mL) | Vinyl (mol %) | Internal (mol %) | Trisubstituted (mol %) | Vinylidene (mol %) | Mn ($^1$H NMR) |
|---|---|---|---|---|---|---|---|---|
| 2 | — | 20.0 | — | 40.4 | 8.9 | 24.3 | 26.4 | 202.6 |
| 3 | 2.0 | 18.0 | 0.0 | 0.0 | 47.0 | 47.3 | 5.7 | 352.5 |
| 4 | 2.0 | 18.0 | 2.5 | 0.0 | 32.2 | 14.6 | 53.2 | 245.8 |
| 5 | 2.0 | 18.0 | 8.0 | 39.9 | 9.0 | 25.1 | 25.9 | 203.0 |

The invention is described above with reference to numerous aspects and specific examples. Many variations will suggest themselves to those skilled in the art in light of the above detailed description. All such obvious variations are within the full intended scope of the appended claims. Other aspects of the invention can include, but are not limited to, the following (aspects are described as "comprising" but, alternatively, can "consist essentially of" or "consist of"):

Aspect 1. A process comprising:

(a) contacting a first olefin feedstock comprising a first $C_4$-$C_{20}$ alpha-olefin with a first catalyst system in a first reaction zone to form a first oligomer product;

(b) discharging a first reaction zone effluent comprising the first oligomer product from the first reaction zone;

(c) optionally deactivating the first catalyst system to form a deactivated first catalyst system, and isolating an effluent fraction by removing at least a portion of the first catalyst system or the deactivated first catalyst system from the first reaction zone effluent;

(d) isolating the first oligomer product by removing at least a portion of unreacted first $C_4$-$C_{20}$ alpha-olefin from the effluent fraction;

(e) contacting a suspension of a second chemically treated solid oxide in a liquid medium, a second metallocene compound, a second organoaluminum compound, and a second olefin feedstock comprising a second $C_4$-$C_{20}$ alpha-olefin, in a second reaction zone to form a second oligomer product, wherein the liquid medium comprises at least a portion of the effluent fraction and/or at least a portion of the first oligomer product;

(f) discharging a second reaction zone effluent comprising the second oligomer product from the second reaction zone, the second oligomer product comprising a light fraction comprising $C_{26}$ and lower oligomers, and a heavy oligomer product comprising $C_{28}$ and higher oligomers;

(g) isolating the heavy oligomer product from the second oligomer product; and (h) hydrogenating at least a portion of the heavy oligomer product to produce a hydrogenated heavy oligomer product.

Aspect 2. The process defined in aspect 1, wherein the liquid medium comprises at least a portion of the effluent fraction.

Aspect 3. The process defined in aspect 1, wherein the liquid medium comprises at least a portion of the first oligomer product.

Aspect 4. A process comprising:

(A) contacting a first olefin feedstock comprising a first $C_4$-$C_{20}$ alpha-olefin with a first catalyst system in a first reaction zone to form a first oligomer product;

(B) discharging a first reaction zone effluent comprising the first oligomer product from the first reaction zone, the first oligomer product comprising a first light fraction comprising $C_{26}$ and lower oligomers, and a first heavy oligomer product comprising $C_{28}$ and higher oligomers;

(C) isolating the first light fraction and isolating the first heavy oligomer product from the first oligomer product;

(D) hydrogenating at least a portion of the first heavy oligomer product to produce a first hydrogenated heavy oligomer product;

(E) contacting a suspension of a second chemically-treated solid oxide in a liquid medium, a second metallocene compound, a second organoaluminum compound, and a second olefin feedstock comprising a second $C_4$-$C_{20}$ alpha-olefin, in a second reaction zone to form a second oligomer product, wherein the liquid medium comprises at least a portion of one or more of the first light fraction, the first heavy oligomer product, the first hydrogenated heavy oligomer product, or any combination thereof;

(F) discharging a second reaction zone effluent comprising the second oligomer product from the second reaction zone, the second oligomer product comprising a second light fraction comprising $C_{26}$ and lower oligomers, and a second heavy oligomer product comprising $C_{28}$ and higher oligomers;

(G) isolating the second heavy oligomer product from the second oligomer product; and (H) hydrogenating at least a portion the second heavy oligomer product to produce a second hydrogenated heavy oligomer product.

Aspect 5. The process defined in aspect 4, wherein the liquid medium comprises at least a portion of the first light fraction.

Aspect 6. The process defined in aspect 4, wherein the liquid medium comprises at least a portion of the first heavy oligomer product.

Aspect 7. The process defined in aspect 4, wherein the liquid medium comprises at least a portion of the first hydrogenated heavy oligomer product.

Aspect 8. The process defined in any one of the preceding aspects, wherein the liquid medium has a 100° C. kinematic viscosity in any range of 100° C. kinematic viscosities disclosed herein, e.g., from 2 to 200 cSt, from 2 to 150 cSt, from 4 to 150 cSt, from 4 to 15 cSt, from 60 to 150 cSt, etc.

Aspect 9. The process defined in any one of the preceding aspects, wherein the suspension comprises an amount of the second chemically-treated solid oxide in any range disclosed herein, e.g., from 1 to 30 wt. %, from 2 to 20 wt. %, from 5 to 15 wt. %, etc., based on the total weight of the second chemically-treated solid oxide and the liquid medium.

Aspect 10. The process defined in any one of aspects 1-9, wherein in step (e) and/or step (E), the suspension of the second chemically-treated solid oxide in the liquid medium, the second metallocene compound, and the second organoaluminum compound are introduced separately to the second reaction zone.

Aspect 11. The process defined in any one of aspects 1-9, wherein in step (e) and/or step (E), at least two of the suspension of the second chemically-treated solid oxide in the liquid medium, the second metallocene compound, and the second organoaluminum compound are combined prior to being introduced to the second reaction zone.

Aspect 12. The process defined in any one of aspects 1-9, wherein step (e) and/or step (E) comprise(s):

i) contacting the suspension of the second chemically-treated solid oxide in the liquid medium with the second organoaluminum compound for a precontact time to form a precontacted mixture;

ii) contacting the precontacted mixture with the second metallocene compound to form a second metallocene-based catalyst system; and iii) contacting the second metallocene-based catalyst system with the second olefin feedstock in the second reaction zone to form the second oligomer product.

Aspect 13. The process defined in aspect 12, wherein step ii) comprises contacting the precontacted mixture with the second metallocene compound and an additional organoaluminum compound.

Aspect 14. The process defined in any one of aspects 1-9, wherein step (e) and/or step (E) comprise(s):

i) contacting the suspension of the second chemically-treated solid oxide in the liquid medium with the second organoaluminum compound for a precontact time to form a precontacted mixture;

ii) introducing the precontacted mixture and the second metallocene compound separately to the second reaction zone; and iii) contacting the precontacted mixture and the second metallocene compound with the second olefin feedstock in the second reaction zone to form the second oligomer product.

Aspect 15. The process defined in any one of the preceding aspects, wherein a storage time of the suspension (prior to contacting with any of the second metallocene compound, the second organoaluminum compound, and the second olefin feedstock) and the precontact time independently comprise a time period in any range of time periods disclosed herein, e.g., from about 10 sec to about 48 hr, from about 30 sec to about 6 hr, at least about 5 sec, at least about 1 min, etc.

Aspect 16. The process defined in any one of the preceding aspects, wherein the second metallocene compound is present as a solution in a solvent or a solid in a diluent.

Aspect 17. The process defined in any one of the preceding aspects, wherein the suspension of the second chemically-treated solid oxide, the second metallocene compound, and the second organoaluminum compound, independently, are periodically or continuously introduced to the second reaction zone, and the second reaction zone effluent is periodically or continuously discharged from the second reaction zone.

Aspect 18. The process defined in any one of the preceding aspects, wherein the first catalyst system is periodically or continuously introduced to the first reaction zone, and the first reaction zone effluent is periodically or continuously discharged from the first reaction zone.

Aspect 19. The process defined in any one of aspects 1-18, wherein the first catalyst system comprises any suitable catalyst system, or any catalyst system disclosed herein, e.g., comprising a Lewis acid; an acidic ionic liquid; a clay, an acidic clay, or an acid washed clay; an acidic ion exchange resin; etc., or any combination thereof.

Aspect 20. The process defined in any one of aspects 1-18, wherein the first catalyst system comprises any suitable metallocene-based catalyst system, or any metallocene-based catalyst system disclosed herein.

Aspect 21. The process defined in any one of aspects 1-18, wherein the first catalyst system comprises a first metallocene compound and an aluminoxane compound.

Aspect 22. The process defined in any one of aspects 1-18, wherein the first catalyst system comprises a first metallocene compound, a first chemically-treated solid oxide, and a first organoaluminum compound.

Aspect 23. The process defined in any one of aspects 21-22, wherein the first metallocene compound is present as a solution in a solvent or a solid in a diluent.

Aspect 24. The process defined in any one of aspects 1-23, wherein the first chemically-treated solid oxide and the second chemically-treated solid oxide are the same or different and independently comprise a solid oxide treated with an electron-withdrawing anion, wherein the solid oxide comprises any solid oxide disclosed herein, e.g., silica, alumina, silica-alumina, silica-coated alumina, aluminum phosphate, aluminophosphate, heteropolytungstate, titania, zirconia, magnesia, boria, zinc oxide, a mixed oxide thereof, or any mixture thereof and the electron-withdrawing anion comprises any electron-withdrawing anion disclosed herein, e.g., sulfate, bisulfate, fluoride, chloride, bromide, iodide, fluorosulfate, fluoroborate, phosphate, fluorophosphate, trifluoroacetate, triflate, fluorozirconate, fluorotitanate, phospho-tungstate, or any combination thereof.

Aspect 25. The process defined in any one of aspects 1-24, wherein the first chemically-treated solid oxide and the second chemically-treated solid oxide are the same or different and independently comprise a fluorided solid oxide, a sulfated solid oxide, or any combination thereof.

Aspect 26. The process defined in any one of aspects 1-24, wherein the first chemically-treated solid oxide and the second chemically-treated solid oxide are the same or different and independently comprise fluorided alumina, chlorided alumina, bromided alumina, sulfated alumina, fluorided silica-alumina, chlorided silica-alumina, bromided silica-alumina, sulfated silica-alumina, fluorided silica-zirconia, chlorided silica-zirconia, bromided silica-zirconia, sulfated silica-zirconia, fluorided silica-titania, fluorided silica-coated alumina, fluorided-chlorided silica-coated alumina, sulfated silica-coated alumina, phosphated silica-coated alumina, or any combination thereof.

Aspect 27. The process defined in any one of aspects 1-26, wherein the first chemically-treated solid oxide and the second chemically-treated solid oxide are the same or different and independently comprise fluorided alumina, sulfated alumina, fluorided silica-alumina, sulfated silica-alumina, fluorided silica-coated alumina, fluorided-chlorided silica-coated alumina, sulfated silica-coated alumina, or any combination thereof.

Aspect 28. The process defined in any one of aspects 1-27, wherein the first chemically-treated solid oxide and the second chemically-treated solid oxide comprise fluorided silica-alumina.

Aspect 29. The process defined in any one of aspects 1-27, wherein the first chemically-treated solid oxide and the second chemically-treated solid oxide comprise fluorided silica-coated alumina.

Aspect 30. The process defined in any one of aspects 1-27, wherein the first chemically-treated solid oxide and the second chemically-treated solid oxide comprise sulfated alumina.

Aspect 31. The process defined in any one of aspects 1-30, wherein the first metallocene compound and the second metallocene compound are the same or different and independently comprise any suitable metallocene compound or any metallocene compound disclosed herein.

Aspect 32. The process defined in any one of aspects 1-31, wherein the first metallocene compound and the second metallocene compound are the same or different and independently comprise a bridged zirconium or hafnium based metallocene compound.

Aspect 33. The process defined in any one of aspects 1-31, wherein the first metallocene compound and the second metallocene compound are the same or different and independently comprise a bridged zirconium based metallocene with a cyclopentadienyl group and a carbon bridging atom or a silicon bridging atom.

Aspect 34. The process defined in any one of aspects 1-31, wherein the first metallocene compound and the second metallocene compound are the same or different and independently comprise an unbridged zirconium or hafnium based metallocene compound containing two cyclopentadienyl groups, two indenyl groups, or a cyclopentadienyl group and an indenyl group.

Aspect 35. The process defined in any one of aspects 1-31, wherein the first metallocene compound and the second metallocene compound are the same or different and independently comprise an unbridged zirconium based metallocene compound containing two cyclopentadienyl groups.

Aspect 36. The process defined in aspect 35, wherein the cyclopentadienyl groups are alkyl-substituted cyclopentadienyl groups.

Aspect 37. The process defined in any one of aspects 1-31, wherein the first metallocene compound and the second metallocene compound are the same or different and independently comprise an unbridged zirconium based metallocene compound containing two indenyl groups.

Aspect 38. The process defined in any one of aspects 1-31, wherein the first metallocene compound and the second metallocene compound are the same or different and independently comprise an unbridged zirconium based metallocene compound containing a cyclopentadienyl group and an indenyl group.

Aspect 39. The process defined in any one of aspects 1-31, wherein the first metallocene compound and the second metallocene compound are the same or different and independently comprise an unbridged zirconium based metallocene compound containing a cyclopentadienyl group and an indenyl group with an alkenyl substituent.

Aspect 40. The process defined in any one of aspects 1-39, wherein the first organoaluminum compound, the second organoaluminum compound, and the additional organoaluminum compound are the same or different and independently comprise any suitable organoaluminum compound or any organoaluminum disclosed herein (e.g., a trialkylaluminum).

Aspect 41. The process defined in any one of aspects 1-40, wherein the first organoaluminum compound, the second organoaluminum compound, and the additional organoaluminum compound are the same or different and independently comprise trimethylaluminum, triethylaluminum, triisobutylaluminum, or any combination thereof.

Aspect 42. The process defined in any one of aspects 1-20 or 22-41, wherein the first catalyst system and the second metallocene-based catalyst system are the same or different and are substantially free of aluminoxane compounds, organoboron or organoborate compounds, ionizing ionic compounds, or any combination thereof.

Aspect 43. The process defined in any one of aspects 1-42, wherein a weight ratio of the (first or second) chemically-treated solid oxide to the (first or second) metallocene compound is in any range of weight ratios disclosed herein, e.g., from 20:1 to 1500:1, from 50:1 to 1500:1, from 50:1 to 1000:1, from 50:1 to 800:1, from 60:1 to 800:1, from 60:1 to 600:1, from 70:1 to 600:1, from 70:1 to 500:1, etc.

Aspect 44. The process defined in any one of aspects 1-43, wherein a molar ratio of aluminum of the (first or second) organoaluminum compound to transition metal of the (first or second) metallocene compound is in any range of molar ratios disclosed herein, e.g., from 5:1 to 5000:1, from 5:1 to 1000:1, from 5:1 to 250:1, from 10:1 to 150:1, etc.

Aspect 45. The process defined in any one of aspects 1-44, wherein a molar ratio of alpha-olefins of the (first or second) olefin feedstock to the (first or second) metallocene compound is in any range of molar ratios disclosed herein, e.g., from $1 \times 10^3:1$ to $1 \times 10^9:1$, from $1 \times 10^4:1$ to $1 \times 10^8:1$, from $1 \times 10^5:1$ to $1 \times 10^7:1$, from $1 \times 10^5:1$ to $1 \times 10^6:1$, etc.

Aspect 46. The process defined in any one of aspects 1-45, wherein the first olefin feedstock and the second olefin feedstock are the same or different and independently comprise any suitable $C_4$-$C_{20}$ alpha-olefin or any $C_4$-$C_{20}$ alpha-olefin disclosed herein, including any mixture or combination thereof.

Aspect 47. The process defined in any one of aspects 1-46, wherein the first olefin feedstock and the second olefin feedstock are the same or different and independently comprise any suitable amount of the $C_4$-$C_{20}$ alpha-olefin or an amount of the $C_4$-$C_{20}$ alpha-olefin in any range disclosed herein, e.g., at least 50 wt. %, at least 70 wt. %, at least 80 wt. %, at least 90 wt. %, at least 95 wt. %, from 50 to 100 wt. %, from 80 to 100 wt. %, from 80 to 98 wt. %, etc.

Aspect 48. The process defined in any one of aspects 1-47, wherein the first olefin feedstock and the second olefin feedstock are the same or different and independently comprise a $C_6$-$C_{18}$ alpha-olefin, a $C_6$-$C_{14}$ alpha-olefin, or a $C_8$-$C_{12}$ alpha-olefin.

Aspect 49. The process defined in any one of aspects 1-48, wherein the first olefin feedstock and the second olefin feedstock are the same or different and independently comprise a $C_6$-$C_{18}$ normal alpha-olefin, a $C_6$-$C_{14}$ normal alpha-olefin, or a $C_8$-$C_{12}$ normal alpha-olefin.

Aspect 50. The process defined in any one of aspects 1-49, wherein the first olefin feedstock and the second olefin feedstock are the same or different and independently comprise 1-hexene, 1-octene, 1-decene, 1-dodecene, 1-tetradecene, 1-hexadecene, or any combination thereof; alternatively, 1-octene, 1-decene, 1-dodecene, or any combination thereof; alternatively, 1-hexene; alternatively, 1-octene; alternatively, 1-decene, alternatively, 1-dodecene; alternatively, 1-tetradecene; or alternatively, 1-hexadecene.

Aspect 51. The process defined in any one of aspects 1-50, wherein the first oligomer product and the second oligomer product are the same or different and are formed, independently, at any suitable oligomerization temperature or at an oligomerization temperature in any range disclosed herein, e.g., from 0° C. to 250° C., from 15° C. to 225° C., from 20° C. to 180° C., from 15° C. to 70° C., from 30° C. to 80° C., etc.

Aspect 52. The process defined in any one of aspects 1-51, wherein the first oligomer product and the second oligomer product are the same or different and are formed, independently, at any suitable reaction pressure or at a reaction pressure in any range disclosed herein, e.g., from atmospheric pressure to 4,000 psig (27.6 MPag), from 1 psig (6.9 kPag) to 3,000 psig (20.9 MPag), from 5 psig (34 kPag) to 2,000 psig (13.8 MPag), from 100 psig (689 kPag) to 1,500 psig (10.3 MPag), etc.

Aspect 53. The process defined in any one of aspects 1-52, wherein the first oligomer product and the second oligomer product are the same or different and are formed, independently, in the presence of any suitable amount of hydrogen or at a hydrogen partial pressure in any range disclosed herein, e.g., from 1 psig (6.9 kPag) to 2000 psig (13.8 MPag), from 5 psig (34 kPag) to 1500 psig (10.3 MPag), from 10 psig (69 kPag) to 1000 psig (6.9 MPag), from 10 psig (69 kPag) to 500 psig (3.5 MPag), from 25 psig (172 kPag) to 500 psig (3.4 MPag), etc.

Aspect 54. The process defined in any one of aspects 1-52, wherein the first oligomer product and the second oligomer product are the same or different and are formed, independently, in the substantial absence of hydrogen (e.g., no added hydrogen).

Aspect 55. The process defined in any one of aspects 1-54, wherein the activity of the (first or second) catalyst system is at least 25,000, at least 30,000, at least 35,000, or at least 40,000 grams of (first or second) oligomer product per gram of (first or second) metallocene compound per hour.

Aspect 56. The process defined in any one of aspects 1-55, wherein the first reaction zone and the second reaction zone are the same or different and comprise, independently, any suitable reactor or any reactor disclosed herein, e.g., a fixed bed reactor, a stirred tank reactor, a plug flow reactor, a loop slurry reactor, etc., or any combination thereof.

Aspect 57. The process defined in any one of aspects 1-56, wherein any isolating step, independently, comprises any suitable technique or any technique disclosed herein, e.g., a filtration process, a flash process, a distillation process, etc., or any combination thereof.

Aspect 58. The process defined in any one of aspects 1-57, wherein the process comprises a step of deactivating the (first or second) catalyst system using any suitable technique or any technique disclosed herein.

Aspect 59. The process defined in any one of aspects 1-58, wherein hydrogenating the heavy oligomer product, the first heavy oligomer product, and the second heavy oligomer product, independently, comprises any suitable hydrogenation technique or any hydrogenation technique disclosed herein.

Aspect 60. The process defined in any one of aspects 1-59, wherein the hydrogenated heavy oligomer product, the first hydrogenated heavy oligomer product, and the second hydrogenated heavy oligomer product are the same or different and comprise, independently:
i) less than 0.5 wt. % hydrogenated monomer,
ii) less than 5 wt. % hydrogenated $C_{26}$ and lower oligomers, and
iii) at least 80 wt. % hydrogenated $C_{28}$ and higher oligomers.

Aspect 61. The process defined in any one of aspects 1-59, wherein the hydrogenated heavy oligomer product, the first hydrogenated heavy oligomer product, and the second hydrogenated heavy oligomer product are the same or different and comprise, independently:
i) less than 0.2 wt. % hydrogenated monomer,
ii) less than 1 wt. % hydrogenated $C_{26}$ and lower oligomers, and
iii) at least 90 wt. % hydrogenated $C_{28}$ and higher oligomers.

Aspect 62. A hydrogenated heavy oligomer product, a first hydrogenated heavy oligomer product, and/or a second hydrogenated heavy oligomer product, produced by the process defined in any one of aspects 1-61.

Aspect 63. A suspension composition comprising:
a $C_4$-$C_{20}$ alpha-olefin oligomer product; and
from 1 to 30 wt. % of a chemically-treated solid oxide.

Aspect 64. The composition defined in aspect 63, wherein the suspension composition comprises an amount of the chemically-treated solid oxide in any range disclosed herein, e.g., from 2 to 20 wt. %, from 5 to 15 wt. %, etc., based on the total weight of the composition.

Aspect 65. The composition defined in any one of aspects 63-64, wherein the composition further comprises an organoaluminum compound.

Aspect 66. The composition defined in any one of aspects 63-65, wherein the composition is substantially free of a metallocene compound.

Aspect 67. The composition defined in any one of aspects 63-66, wherein the alpha-olefin oligomer product has a 100° C. kinematic viscosity in any range of 100° C. kinematic viscosities disclosed herein, e.g., from 2 to 200 cSt, from 2 to 150 cSt, from 4 to 150 cSt, from 4 to 15 cSt, from 60 to 150 cSt, etc.

Aspect 68. The composition defined in any one of aspects 63-67, wherein the alpha-olefin oligomer product comprises at least 80 wt. %, at least 90 wt. %, or at least 95 wt. %, of a light fraction comprising $C_{26}$ and lower oligomers.

Aspect 69. The composition defined in any one of aspects 63-67, wherein the alpha-olefin oligomer product comprises at least 80 wt. %, at least 90 wt. %, or at least 95 wt. %, of a heavy oligomer product comprising $C_{28}$ and higher oligomers.

Aspect 70. The composition defined in any one of aspects 63-67, wherein the alpha-olefin oligomer product comprises at least 80 wt. %, at least 90 wt. %, or at least 95 wt. %, of a hydrogenated heavy oligomer product comprising hydrogenated $C_{28}$ and higher oligomers.

Aspect 71. The composition defined in any one of aspects 63-67, wherein the alpha-olefin oligomer product comprises at least 80 wt. %, at least 90 wt. %, or at least 95 wt. %, of an effluent fraction comprising $C_4$-$C_{20}$ alpha-olefin monomer, a light fraction comprising $C_{26}$ and lower oligomers, and a heavy oligomer product comprising $C_{28}$ and higher oligomers.

Aspect 72. The composition defined in any one of aspects 63-67, wherein the alpha-olefin oligomer product comprises at least 80 wt. %, at least 90 wt. %, or at least 95 wt. %, of an oligomer product comprising a light fraction comprising $C_{26}$ and lower oligomers, and a heavy oligomer product comprising $C_{28}$ and higher oligomers.

We claim:
1. A process comprising:
(a) contacting a first olefin feedstock comprising a first $C_4$-$C_{20}$ alpha-olefin with a first catalyst system in a first reaction zone to form a first oligomer product;
(b) discharging a first reaction zone effluent comprising the first oligomer product from the first reaction zone;
(c) (i) isolating an effluent fraction by removing at least a portion of the first catalyst system from the first reaction zone effluent, or (ii) deactivating the first catalyst system to form a deactivated first catalyst system, and isolating an effluent fraction by removing at least a portion of the deactivated first catalyst system from the first reaction zone effluent;
(d) isolating the first oligomer product by removing at least a portion of unreacted first $C_4$-$C_{20}$ alpha-olefin from the effluent fraction;
(e) contacting a suspension of a second chemically-treated solid oxide in a liquid medium, a second metallocene compound, a second organoaluminum compound, and a second olefin feedstock comprising a second $C_4$-$C_{20}$ alpha-olefin, in a second reaction zone to form a second oligomer product, wherein the liquid medium comprises at least a portion of the effluent fraction and/or at least a portion of the first oligomer product;

(f) discharging a second reaction zone effluent comprising the second oligomer product from the second reaction zone, the second oligomer product comprising a light fraction comprising $C_{26}$ and lower oligomers, and a heavy oligomer product comprising $C_{28}$ and higher oligomers;

(g) isolating the heavy oligomer product from the second oligomer product; and (h) hydrogenating at least a portion of the heavy oligomer product to produce a hydrogenated heavy oligomer product.

2. The process of claim 1, wherein:
the liquid medium comprises at least a portion of the effluent fraction;
the effluent fraction has a 100° C. kinematic viscosity in a range from 3 to 200 cSt; and
the suspension comprises from 2 to 20 wt. % of the second chemically-treated solid oxide.

3. The process of claim 1, wherein:
the liquid medium comprises at least a portion of the first oligomer product;
the first oligomer product has a 100° C. kinematic viscosity in a range from 2 to 150 cSt; and
the suspension comprises from 5 to 15 wt. % of the second chemically-treated solid oxide.

4. The process of claim 1, wherein in step (e), at least two of the suspension of the second chemically-treated solid oxide in the liquid medium, the second metallocene compound, and the second organoaluminum compound are combined prior to being introduced to the second reaction zone.

5. The process of claim 1, wherein step (e) comprises:
i) contacting the suspension of the second chemically-treated solid oxide in the liquid medium with the second organoaluminum compound for a precontact time to form a precontacted mixture;
ii) contacting the precontacted mixture with the second metallocene compound to form a second metallocene-based catalyst system; and
iii) contacting the second metallocene-based catalyst system with the second olefin feedstock in the second reaction zone to form the second oligomer product.

6. The process of claim 1, wherein step (e) comprises:
i) contacting the suspension of the second chemically-treated solid oxide in the liquid medium with the second organoaluminum compound for a precontact time to form a precontacted mixture;
ii) introducing the precontacted mixture and the second metallocene compound separately to the second reaction zone; and
iii) contacting the precontacted mixture and the second metallocene compound with the second olefin feedstock in the second reaction zone to form the second oligomer product.

7. The process of claim 1, wherein the first catalyst system comprises a first metallocene compound and an aluminoxane compound.

8. The process of claim 1, wherein the first catalyst system comprises a first metallocene compound, a first chemically-treated solid oxide, and a first organoaluminum compound.

9. The process of claim 8, wherein:
the first metallocene compound and the second metallocene compound are the same and comprise an unbridged zirconium or hafnium based metallocene compound containing two cyclopentadienyl groups, two indenyl groups, or a cyclopentadienyl group and an indenyl group;
the first chemically-treated solid oxide and the second chemically-treated solid oxide are the same and comprise a fluorided solid oxide, a sulfated solid oxide, or any combination thereof; and
the first organoaluminum compound and the second organoaluminum compound are the same and comprise trimethylaluminum, triethylaluminum, triisobutylaluminum, or any combination thereof.

10. The process of claim 8, wherein:
the first olefin feedstock comprises at least 80 wt. % of $C_6$ to $C_{14}$ alpha olefins; and
the second olefin feedstock comprises at least 80 wt. % of $C_8$ to $C_{12}$ alpha olefins.

11. The process of claim 1, wherein the first olefin feedstock and the second olefin feedstock are the same or different and independently comprise 1-hexene, 1-octene, 1-decene, 1-dodecene, 1-tetradecene, 1-hexadecene, or any combination thereof.

12. The process of claim 1, wherein:
the first reaction zone and the second reaction zone are the same and comprise a fixed bed reactor, a stirred tank reactor, a plug flow reactor, a loop slurry reactor, or any combination thereof;
each isolating step, independently, comprises a filtration process, a flash process, a distillation process, or any combination thereof; and
the hydrogenated heavy oligomer product comprises:
  i) less than 0.5 wt. % hydrogenated monomer,
  ii) less than 5 wt. % hydrogenated $C_{26}$ and lower oligomers, and
  iii) at least 80 wt. % hydrogenated $C_{28}$ and higher oligomers.

13. A process comprising:
(A) contacting a first olefin feedstock comprising a first $C_4$-$C_{20}$ alpha-olefin with a first catalyst system in a first reaction zone to form a first oligomer product;
(B) discharging a first reaction zone effluent comprising the first oligomer product from the first reaction zone, the first oligomer product comprising a first light fraction comprising $C_{26}$ and lower oligomers, and a first heavy oligomer product comprising $C_{28}$ and higher oligomers;
(C) isolating the first light fraction and isolating the first heavy oligomer product from the first oligomer product;
(D) hydrogenating at least a portion of the first heavy oligomer product to produce a first hydrogenated heavy oligomer product;
(E) contacting a suspension of a second chemically-treated solid oxide in a liquid medium, a second metallocene compound, a second organoaluminum compound, and a second olefin feedstock comprising a second $C_4$-$C_{20}$ alpha-olefin, in a second reaction zone to form a second oligomer product, wherein the liquid medium comprises at least a portion of one or more of the first light fraction, the first heavy oligomer product, the first hydrogenated heavy oligomer product, or any combination thereof;
(F) discharging a second reaction zone effluent comprising the second oligomer product from the second reaction zone, the second oligomer product comprising a second light fraction comprising $C_{26}$ and lower oligomers, and a second heavy oligomer product comprising $C_{28}$ and higher oligomers;
(G) isolating the second heavy oligomer product from the second oligomer product; and (H) hydrogenating at least a portion the second heavy oligomer product to produce a second hydrogenated heavy oligomer product.

14. The process of claim 13, wherein:
the liquid medium comprises at least a portion of the first light fraction;
the first light fraction has a 100° C. kinematic viscosity less than or equal to 10 cSt; and
the suspension comprises from 2 to 20 wt. % of the second chemically-treated solid oxide.

15. The process of claim 13, wherein:
the liquid medium comprises at least a portion of the first heavy oligomer product;
the first heavy oligomer product has a 100° C. kinematic viscosity in a range from 2 to 200 cSt; and
the suspension comprises from 5 to 15 wt. % of the second chemically-treated solid oxide.

16. The process of claim 13, wherein:
the liquid medium comprises at least a portion of the first hydrogenated heavy oligomer product;
the first hydrogenated heavy oligomer product has a 100° C. kinematic viscosity in a range from 2 to 200 cSt; and
the suspension comprises from 1 to 30 wt. % of the second chemically-treated solid oxide.

17. The process of claim 13, wherein the first hydrogenated heavy oligomer product and the second hydrogenated heavy oligomer product are the same or different and comprise, independently:
i) less than 0.2 wt. % hydrogenated monomer,
ii) less than 1 wt. % hydrogenated $C_{26}$ and lower oligomers, and
iii) at least 90 wt. % hydrogenated $C_{28}$ and higher oligomers.

18. The process of claim 1, wherein:
the liquid medium comprises at least a portion of the first oligomer product;
the first oligomer product has a 100° C. kinematic viscosity in a range from 60 to 200 cSt; and
the suspension comprises from 2 to 20 wt. % of the second chemically-treated solid oxide.

19. The process of claim 18, wherein:
the second chemically-treated solid oxide comprises a fluorided solid oxide, a sulfated solid oxide, or any combination thereof;
the second organoaluminum compound comprises trimethylaluminum, triethylaluminum, triisobutylaluminum, or any combination thereof; and
the second olefin feedstock comprises at least 80 wt. % of 1-hexene, 1-octene, 1-decene, 1-dodecene, 1-tetradecene, 1-hexadecene, or any combination thereof.

20. The process of claim 19, wherein:
the 100° C. kinematic viscosity is in a range from 60 to 150 cSt; and
the suspension comprises from 5 to 18 wt. % of the second chemically-treated solid oxide.

21. The process of claim 13, wherein:
the liquid medium comprises at least a portion of the first light fraction; and
the suspension comprises from 5 to 18 wt. % of the second chemically-treated solid oxide.

22. The process of claim 21, wherein:
the second chemically-treated solid oxide comprises a fluorided solid oxide, a sulfated solid oxide, or any combination thereof;
the second organoaluminum compound comprises trimethylaluminum, triethylaluminum, triisobutylaluminum, or any combination thereof; and
the second olefin feedstock comprises at least 80 wt. % of 1-hexene, 1-octene, 1-decene, 1-dodecene, 1-tetradecene, 1-hexadecene, or any combination thereof.

* * * * *